US007338762B2

(12) United States Patent
Gorenstein et al.

(10) Patent No.: US 7,338,762 B2
(45) Date of Patent: Mar. 4, 2008

(54) BEAD BOUND COMBINATORIAL OLIGONUCLEOSIDE PHOSPHOROTHIOATE AND PHOSPHORODITHIOATE APTAMER LIBRARIES

(75) Inventors: David G. Gorenstein, Houston, TX (US); Xianbin Yang, Webster, TX (US); Bruce A. Luxon, Galveston, TX (US); Norbert Herzog, Friendswood, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 117 days.

(21) Appl. No.: 10/828,935

(22) Filed: Apr. 21, 2004

(65) Prior Publication Data

US 2005/0123939 A1    Jun. 9, 2005

Related U.S. Application Data

(63) Continuation-in-part of application No. 10/272,509, filed on Oct. 16, 2002.

(60) Provisional application No. 60/334,887, filed on Nov. 15, 2001.

(51) Int. Cl.
*C12Q 1/68* (2006.01)
*C07K 7/00* (2006.01)

(52) U.S. Cl. ............ 435/6; 435/5; 435/4; 435/DIG. 14; 435/DIG. 17; 536/23.1; 536/1.1

(58) Field of Classification Search .................. 435/6, 435/5, 4; 536/23.1
See application file for complete search history.

(56) References Cited

U.S. PATENT DOCUMENTS

| 5,218,088 | A | 6/1993 | Gorensein |
| 5,270,163 | A | 12/1993 | Gold et al. |
| 5,397,698 | A | 3/1995 | Goodman |
| 5,475,096 | A | 12/1995 | Gold et al. |
| 5,576,302 | A | 11/1996 | Cook |
| 5,582,981 | A | 12/1996 | Toole et al. |
| 5,587,361 | A | 12/1996 | Cook |
| 5,599,797 | A | 2/1997 | Cook |
| 5,602,000 | A | 2/1997 | Hyman |
| 5,607,923 | A | 3/1997 | Cook |
| 5,620,963 | A | 4/1997 | Cook |
| 5,635,488 | A | 6/1997 | Cook |
| 5,639,603 | A | 6/1997 | Dower et al. |
| 5,639,873 | A | 6/1997 | Barascut |
| 5,660,985 | A | 8/1997 | Pieken |
| 5,661,134 | A | 8/1997 | Cook |
| 5,663,153 | A | 9/1997 | Hutcherson et al. |
| 5,668,265 | A | 9/1997 | Nadeau et al. |
| 5,670,637 | A | 9/1997 | Gold et al. |
| 5,696,249 | A | 12/1997 | Gold et al. |
| 5,705,337 | A | 1/1998 | Gold |
| 5,734,041 | A | 3/1998 | Just |
| 5,756,291 | A | 5/1998 | Griffin et al. |
| 5,763,595 | A | 6/1998 | Gold |
| 5,795,721 | A | 8/1998 | Rabin |
| 5,801,154 | A | 9/1998 | Baracchini et al. |
| 5,804,445 | A | 9/1998 | Brasier |
| 5,844,106 | A | 12/1998 | Seela et al. |
| 5,853,984 | A | 12/1998 | Davis |
| 5,874,219 | A | 2/1999 | Rava |
| 6,171,792 | B1 | 1/2001 | Brent et al. |
| 6,180,348 | B1 | 1/2001 | Li |
| 6,242,246 | B1 | 6/2001 | Gold |
| 6,346,611 | B1 | 2/2002 | Pagratis et al. |
| 6,369,208 | B1 | 4/2002 | Cole et al. |
| 6,423,493 | B1 | 7/2002 | Gorenstein |
| 6,458,543 | B1 | 10/2002 | Gold |
| 6,503,715 | B1 | 1/2003 | Gold |
| 6,514,948 | B1 | 2/2003 | Raz et al. |
| 6,544,776 | B1 | 4/2003 | Gold |
| 6,551,795 | B1 | 4/2003 | Rubenfield et al. |
| 6,610,504 | B1 | 8/2003 | Yuan |
| 6,713,616 | B2 | 3/2004 | Pagratis et al. |
| 6,716,629 | B2 * | 4/2004 | Hess et al. .................. 435/420 |
| 6,867,289 | B1 | 3/2005 | Gorenstein et al. |
| 2001/0014461 | A1 | 8/2001 | Hutchens et al. |
| 2001/0014479 | A1 | 8/2001 | Hutchens et al. |
| 2001/0034330 | A1 | 10/2001 | Kensil |
| 2003/0133229 | A1 | 7/2003 | Klinman et al. |
| 2003/0162190 | A1 | 8/2003 | Gorenstein et al. |
| 2003/0162216 | A1 | 8/2003 | Gold |
| 2003/0186906 | A1 | 10/2003 | Schlingensiepen et al. |

FOREIGN PATENT DOCUMENTS

| EP | 0 855 184 A1 | 7/1998 |
| WO | WO 92 14842 A | 9/1992 |
| WO | WO 92 14843 | 9/1992 |

(Continued)

OTHER PUBLICATIONS

Antsypovich, et al. (1998) Cross-linked DNA duplexes: Exonuclease stability and interaction with the nucleic transcription factor of the κ light chain enhancer (NF-κB).

(Continued)

*Primary Examiner*—T. D. Wessendorf
(74) *Attorney, Agent, or Firm*—Edwin Flores; Chalker Flores, LLP

(57) ABSTRACT

The present invention includes composition and methods for making and using a combinatorial library having two or more beads, wherein attached to each bead is a unique nucleic acid aptamer that have disposed thereon a unique sequence. The library aptamers may be attached covalently to the one or more beads, which may be polystyrene beads. The aptamers may include phosphorothioate, phosphorodithioate and/or methylphosphonate linkages and may be single or double stranded DNA, RNA or even PNAs.

18 Claims, 9 Drawing Sheets

FOREIGN PATENT DOCUMENTS

| WO | WO 93 08296 A | 4/1993 |
|---|---|---|
| WO | 94/01550 A1 | 1/1994 |
| WO | WO 96 19572 A | 6/1996 |
| WO | WO 99 31275 | 6/1999 |
| WO | 99/54506 A1 | 10/1999 |
| WO | 00/24404 A1 | 5/2000 |
| WO | WO 00 47774 A1 | 8/2000 |
| WO | WO 96 41019 A1 | 8/2000 |
| WO | 2004/026260 A2 | 4/2004 |
| WO | 2005/003291 A2 | 1/2005 |
| WO | 2005/018357 A2 | 3/2005 |
| WO | 2005/032455 A2 | 4/2005 |
| WO | 2005/037053 A2 | 4/2005 |

OTHER PUBLICATIONS

Bielinska, et al. (1990) Regulation of Gene Expression with Double-Stranded Phosphorothioate Oligonucleotides, *Science*, vol. 250, p. 997-1000.

Khaled, et al. (1998) Use of Phosphorothioate-Modified Oligodeozynuceotides to inhibit NF-κB Expression and Lymphocyte Function, *Clinical Immunology and Immunopathology*, vol. 86, No. 2, pp. 170-179.

King, et al., (1998) Novel Combinatorial Selection of Phosphorothioate Oligonucleotide Aptamers. *Biochemistry*, 37, 16489-16493.

Kunsch, et al. (1992) Selection of Optimal κB/Rel DNA-Binding Motifs: Interaction of Both Subunits of NF-κB with DNA is Required for Transcriptional Activation, *Molecular and Cellular Biology*, Oct. 1992, vol. 12, No. 10, p. 4412-4421.

Lebruska, et al. (1999) Selection and Characterization of an RNA Decoy for Transcription Factor NF-κB+, *Biochemistry*, 38, 3168-3174.

Morishita, et al. (1997) In vivo transfection of cis element "decoy" against nuclear factor- κB binding site prevents myocarial infarction, *Nature Medicine*, vol. 3, No. 8, p. 894-899.

Nakamaye, et al. (1988) Direct sequencing of polymerase chain reaction amplified DNA fragments through the incorporation of deoxynucleoside α-thiophosphates, *Nucleic Acids Research*, vol. 16, No. 21.

Sharma, et al. (1996) Transcription Factor Decoy Approach to Decipher the Role of NF-κB in Oncogenesis, *Anticancer Research*, 16:61-70.

Stec, et al. (1997) Deoxyribonucleoside 3'-O-(2-Thio- and 2-Oxo-"spiro"-4,4-pentamethylene-1,3,2-oxathiaphospholane)s: Monomers for Stereocontrolled Synthesis of Oligo(deoxyribonucleoside phosphorothioate)s and Chimeric PS/PO Oligonucleotides§, *J. Am. Chem. Soc.*, 120, 7156-7167.

Uhlmann, et al. (1997) Studies of the Mechanism of Stabilization of Partially Phosphorothioated Oligonucleotides Against Nucleolytic Degradation, *Antisense & nucleic Acid Drug Development*, 7:345-350.

Zon, Gerald (1988) Oligonucleotide Analogues as Potential Chemotherapeutic Agents. Pharmaceutical Research, vol. 5, No. 9, pp. 539-549.

Partial Supplementary European Search Report for Application No. 04776088.9 (PCT/US2004/016246) dated Jun. 29, 2007.

Partial Supplementary European Search Report for Application No. 04809405.6 (PCT/US2004/016061) dated Jul. 3, 2007.

Bane, et al., "DNA affinity capture and protein profiling by SELDI-TOF mass spectrometry: effect of DNA methylation," Nucleic Acids Research (2002), 30:e69.

Dick, et al., "Aptamer-Enhanced Laser Desorption/Ionization of Affinity Mass Spectrometry," Analytical Chemistry (2004), 76:3037-3041.

Wang, et al., "Identification of Proteins Bound to a Thioaptamer Probe on a Proteomics Array," Biochemical and Biophysical Research Communications (2006), 347:586-593.

Amarzguioui, M., et al., Nuc Acids Res, 31, 589-595, (2003)—Tolerance for mutations and chemical modifications in a SiRNA.

Andreola, M., et al., " Towards the Selection of Phosphorothioate Aptamers: Optimizing In Vitro Selection Steps with Phosphorothioate Nucleotides," European Journal of Biochemistry 267:5032-5040.

Braasch, D.A., et al., Nucleic Acids Res, 30(23), 5160-7 (2002)—Antisense inhibition of gene expression in cells by oligonucleotides incorporating locked nucleic acids: effect of mRNA target sequence and chimera design.

Braasch, D.A. and D.R. Corey, Biochemistry, 41, 4503-4510 (2002)—Novel anitsense and peptide nucleic acid strategies for controlling gene expression.

Caplen, N.J., et al., PNAS, 98, 9742-9747 (2001)—Specific inhibition of gene expression by small double-stranded RNAs in invertebrate and vertebrate systems.

Cassiday, L., et al., "In Vivo Recognition of an RNA Aptamer by its Transcription Factor Target," Biochemistry (2001), 40:2433-3438.

Chi, J.T., PNAS,100(11), 6343-6 (2003)—Genomewide view of gene silencing by small interfering RNAs.

Doucette, et al., Proteomics (2001), 1:987-1000, Investigation of the Applicability of a Sequential Digestion Protocol Using Trypsin and Leucine Aminopeptidase M for Protein Identification by Matrix-Assisted Laser Desorption/Ionization—Time of Flight Mass Spectrometry.

Elbashir, et al., "RNA Interference is Mediated by 21- 22-nucleotide RNAs," Genes and Development (2001), 15:188-200.

Elbashir, et al., "Functional Anatomy of SiRNAs for Mediating Efficient RNA1 in *Drosophilia melanogaster* Embryo Lysate," EMBO Journal (2001), 20:6877-6888.

Elgemeie, "Thioguanine Mercaptoputine: Their Analogs and Nucleosides as antimetabolites," Current Pharmaceutical Design (2003), 9:2627-2642.

Fire, et al., Nature, 391, 806 (1998)—Potent and specific genetic interference by dsRNA in C.elegans.

Gitlin, L., et al., Nature, 418, 430-434 (2002)—Short interfering RNA confers intracellular antiviral immunity in human cells.

Hu, W., et al., Curr Biol, 12, 1301-1311 (2002)—Inhibition of retroviral pathogenesis by RNA interference.

Jackson, A.L., et al., Nat Biotech, 21(6), 635-637 (2003)—Expression profiling reveals off-target gene regulation by RNAi.

Jacque, J.M., et al., Nature, 418, 435-438 (2002)—Modulation of HIV-1 replication by RNA interference.

Jansen, B. and U. Zangemeister-Witte, Lancet Oncol, 3, 672-683 (2002)—Antisense therapy for cancer—the time for truth.

Kanaori, et al., "Effect of Phosphorothioate Chiraliy on i-Motif Structure and Stability," Biochemistry (2004), 43:5672-5679.

Kawasaki, H., et al (Taira), Nuc Acids Res, 31(3), 981-987 (2003)—siRNAs generated by recombinant human Dicer include specific and significant but target site-independent gene silencing in human cells.

King, D. et al., "Combinatorial Selection and Binding of Phosphorothioate Aptamers Targeting Human NF-kappa B RelA (p65) and p50," Biochemistry (2002), 41:9696-9706.

King, D.J., "Selection Binding and Design of Phosphorothioate Duplex Aptamers for the Transcription Factors NF-IL6 and NP-KB," dissertation Aug. 2001.

Koller, E., et al., Trends Pharm Sci, 21, 142-148—Elucidating cell signaling mechanisms using antisense technology.

Lescar, J. et al., Cell 105(1), 137-48. (2001)—The fusion glycoprotein shell of Semliki Forest virus: an icosahedral assembly primed for fusogenic activation at endosomal pH.

McCaffrey, A.P., et al., Nat Biotechnol, 21(6), 639-44 (2003)—Inhibition of hepatitis B virus in mice by RNA interference.

Miller, V.M.., et al., PNAS, 100(12), 7195-200—Allele-specific silencing of dominant disease genes.

Novina, C.D., et al., Nat Med, 8, 681-686 (2002)—SiRNA-directed inhibition of HIV-1 infection.

Opalinska, et al., Nature Reviews (2002), 1:503-514., Nucleic-Acid Therapeutics: Basic Principles and Recent Applications.

Parrish, S., et al (Fire research group), Mol Cell, 6, 1077-87 (2001)—Functional anatomy of a dsRNA trigger:differential requirement for the two trigger strands in RNA interference.

Pletnev, S.V., et al., Cell 105(1), 127-36 (2001)—Locations of carbohydrate sites on alphavirus glycoproteins show the E1 forms an icosahedral scaffold.

Raveh, S., "Peptidic Determinants and Structural Model of Human NDP kinase B Bound in Single-Stranded DNA," Biochemistry (2001), 40:5882-5893.

Sazani, et al., "Nuclear Antisense Effects of Neutral Anionic and Cationic Oligonucleotide Analogs," Nucleic Acids Research (2001), 29:3965-3974.

Semizarov, D., et al., PNAS, 100(11), 6347-52 (2003)—Specificity of short interfering RNA determined through gene expression signatures.

Song, E., et al., Nat Med, 9, 347-351 (2003)—RNA interference targeting Fas protects mice from fulminant hepatitis.

Song, E., et al., J Virol. Jul. 2003;77(13):7174-81 (2003)—Sustained small interfering RNA-mediated Human Immunodeficiency Virus Type 1 inhibition in primary macrophages.

Ueda, Takuya, et al. (1991) Phosphorothioate-containing RNAs show mRNA activity in the prokaryotic translation systems in vitro. Nucleic Acids Research, vol. 19, No. 3, pp. 547-552.

Xia, H.B. et al. Nat Biotech, 20, 1006-1010 (2002)—siRNA-mediated gene silencing in vitro and in vivo.

Yang, X., et al., "Construction and Selection of Bead-Bound Combinatorial Olignucleoside Phosphorothioate and Phosphoroditihioate Aptamer Libraries Designed for Rapid PCR-Based Sequencing," Nucleic Acid Research (2002), 30:132-140.

Yokota, T., et al. (Taira), EMBO Rep., 4(6), 602-608 (2003)—Inhibition of intracellular hepatitis C virus by synthetic and vector-derived small interfering RNAs.

Zhang, Haidi, et al. (2004), Single Processing Center Models for Human Dicer and Bacterial RNase III. Cell, vol. 118, pp. 57-68.

* cited by examiner

Antibody based assay screen - fluorigenic

Sequences of individual beads of dithioate library selected for binding to NF-κB

Sequences from screening with fluorescently labeled p50 protein

☐ 1 CGCCAGCCAaAGGTGCTGTCAG
☐ 2 CGCCcAGTgGCTAGTgaACCCC
☐ 3 ATGTAGCCgaAGGTGgaACCCC
☐ 4 CGCCAGCCgaAGGTGgaACCCC

☐ A 10003100133010000330010
☐ C 30331033001000001003433
☐ G 03100310310331330100001
☐ T 01010001000010310101000

CGCCAGCCgaAGGTGgaACCCC

Sequences from immunofluorescence assay

☐ 1 ATGTAGCCAaAGGTGgaACCCC
☐ 2 CGCCAGCCgaAGGTGCTGTCAG
☐ 3 CGCCcAGTgaAGGTGCTGTCAG
☐ 4 CGCCcAGTAGCTAGTCTGTCAG

☐ A 10002200233010001100030
☐ C 30332022001000003001411
☐ G 03100220210331310300003
☐ T 01010002000103103030000

CGCCAGCCgaAGGTGCTGTCAG
CAGTA

Figure 6

BEAD BOUND COMBINATORIAL OLIGONUCLEOSIDE PHOSPHOROTHIOATE AND PHOSPHORODITHIOATE APTAMER LIBRARIES

This application is a continuation in part application based on U.S. patent application Ser. No. 10/272,509, filed Oct. 16, 2002, and a continuation in part of U.S. Provisional Patent Application No. 60/334,887, filed on Nov. 15, 2001.

This work was supported by the following United States Government grants DARPA (9624-107 FP), NIH (AI27744) and NIEHS (ES06676).

TECHNICAL FIELD OF THE INVENTION

The present invention relates in general to the field of aptamer libraries, and more particularly, to enhancing availability and use of aptamers for screening, including high-throughput screening, of primary or secondary target molecules by using thioated aptamers bound to a substrate.

BACKGROUND OF THE INVENTION

Without limiting the scope of the invention, its background is described in connection with oligonucleotide agents and with methods for the isolation of sequences that are bound by nucleic acid binding molecules and the like.

Virtually all organisms have nuclease enzymes that degrade rapidly foreign DNA as an important in vivo defense mechanism. The use, therefore, of normal oligonucleotides as diagnostic or therapeutic agents in the presence of most bodily fluids or tissue samples is generally precluded. It has been shown, however, that phosphoromonothioate or phosphorodithioate modifications of the DNA backbone in oligonucleotides can impart both nuclease resistance and enhance the affinity for target molecules, such as for example the transcriptional regulating protein NF-κB. Thus, from the foregoing, it is apparent there is a need in the art for methods for generating aptamers that have enhanced binding affinity for a target molecule, as well as retained specificity. Also needed are ways to identify and quantify in detail the mechanisms by which aptamers interact with target molecules.

Current DNA array technology is problematic in that it is focused on the identification and quantification of a single mRNA species, and does not provide information on the more relevant level of functional protein expression and in particular protein-protein interactions such as between heterodimers and homodimers. Although microarrays have been used for detecting the proteome, most of these are based on antibodies or normal backbone aptamers.

Synthetic phosphodiester-modified oligonucleotides such as phosphorothioate oligonucleotide (S—ODN) and phosphorodithioate oligonucleotide ($S_2$—ODN) analogues have increased nuclease resistance and may bind to proteins with enhanced affinity. Unfortunately, ODNs possessing high fractions of phosphorothioate or phosphorodithioate linkages may lose some of their specificity and are "stickier" towards proteins in general than normal phosphate esters, an effect often attributed to non-specific interactions. The recognition of nucleic acid sequences by proteins involves specific sidechain and backbone interactions with both the nucleic acid bases as well as the phosphate ester backbone, effects which may be disrupted by the non-specific interactions caused with S—ODN and $S_2$—ODN analogues.

Gorenstein, et al., U.S. Pat. No. 6,423,493, have taken advantage of this "stickiness" to enhance the affinity of S—ODN and $S_2$—ODN agents for a protein target. A screening method was developed to optimize the total number of phosphorothioate or phosphorodithioate linkages that: decreased non-specific binding to the protein target while enhancing only the specific favorable interactions with the target protein.

Other advances in combinatorial chemistry allow construction and screening of large random sequence nucleic acid "aptamer" libraries (e.g., Ellington, A. D. and Szostak, J. W. (1990) In vitro selection of RNA molecules that bind specific ligands. Nature, 346, 818-822); targeting proteins (e.g., Bock, L. C., et al., (1992) Selection of single-stranded DNA molecules that bind and inhibit human thrombin. Nature, 355, 564-566.); and other molecules (Koizumi, M. and Breaker, R. R. (2000) Molecular recognition of cAMP by an RNA aptamer. Biochemistry, 39, 8983-8992; Gold, L., et al. (1997) SELEX and the evolution of genomes. Curr. Opin. Genetic. Dev., 7, 848-851.; and Ye, X., et al. (1996) Deep penetration of an α-helix into the widened RNA major groove in the HIV-1 Rev peptide-RNA aptamer complex. Nat. Struct. Biol., 3, 1026-1033.).

The identification of specific S—ODN and $S_2$—ODN aptamers ("thioaptamers") that bind proteins based upon in vitro combinatorial selection methods, however, is limited to substrates only accepted by polymerases required for reamplification of selected libraries by the polymerase chain reaction (PCR). One disadvantage of using the polymerization of substituted nucleoside 5'-triphosphates into ODN aptamers are the restrictions on the choice of P-chirality by the enzymatic stereospecificity. For example, it is known that $[S_p]$-diastereoisomers of dNTP(αS) in Taq-catalyzed polymerization solely yield $[R_p]$-phosphorothioate stereoisomers (Eckstein, F. (1985) Nucleoside phosphorothioates. Annu. Rev. Biochem., 54, 367-402.). Therefore, using current methods it is not possible to select $[S_p]$-phosphorothioate stereoisomers along with achiral $S_2$—ODN analogous since both $[R_p]$-diastereoisomers of dNTP(αS) and nucleoside dNTP(α$S_2$) are not substrates of polymerases. Additionally, these in vitro combinatorial selection methods require many iterative cycles of selection and reamplification of the bound remaining members of the library by the PCR, which are quite time consuming.

What is needed are compositions and methods that permit the isolation of, e.g., individual aptamer:protein complexes without the need for repeated iterative cycles of selection and reamplification of likely binding targets. Also needed are compositions, methods and systems that permit the creation, isolation, sequencing and characterization of making $[S_p]$-phosphorothioate stereoisomers along with achiral $S_2$—ODN analogs using, e.g., $[R_p]$-diastereoisomers of dNTP(αS) and nucleoside dNTP(α$S_2$). Also needed are methods for creating libraries that permit not only the isolation of a primary aptamer:protein target, but the isolation of protein(s) that may interact with the aptamer:protein target, so called secondary interactions.

SUMMARY OF THE INVENTION

The present invention addressed the problems in the prior art by developing composition and methods for making and using a combinatorial library in which each substrate, e.g., a bead, has attached thereto a unique ODN sequence. More particularly, the one-bead, one-ODN library of the present invention includes two or more beads, wherein attached to each bead is a unique nucleic acid aptamer that have disposed thereon a unique sequence. The bead library aptamers may be attached covalently to the one or more beads, which may be polystyrene beads. The aptamers may include phosphorothioate, phosphorodithioate and/or methylphosphonate linkages and may be single or double stranded DNA, RNA or even PNAs.

The ODNs attached to the substrate or bead or the present invention may also include one or more predetermined nucleic acid sequences, e.g., having at least 10, 12, 16, or more bases. The predetermined sequence may be a 5' nucleic acid sequence, a 3' nucleic acid sequence, and a 5' and a 3' nucleic acid sequence to the ODN. In one embodiment the ODN is attached to, e.g., a polystyrene/polydivinyl benzene copolymer bead with, e.g., a hexaethyleneglycol linker. The aptamers may be isosteric, isopolar and/or achiral. The aptamers may further include a detectable marker, e.g., a colorimetric agent such as a fluorophor. The detectable marker may be attached to the 5' end, the 3' end or internally within the aptamers. The aptamers of the present invention may be single or double stranded.

In another embodiment of the present invention the one-bead, one-ODN combinatorial library includes two or more beads, attached to each bead is a unique aptamer that has a single unique sequence, and each unique aptamer includes a mix of modified and unmodified nucleotides. In one embodiment the aptamer is double stranded and the modifications to each strand is unique and does not mirror the modifications to the complementary strand.

Yet another embodiment of the present invention is an ODN library in which a library substrate has a surface and attached to the library substrate are the individual beads of a one-bead, one-ODN bead library. The library substrate may be, e.g., a bead, a chip, a chip that includes a capacitance-coupled detector, a photolithographically etched microwell plate to contain beads ("Texas tongue") or even a glass slide.

The present invention also includes a method of making a combinatorial library including the steps of: attaching a single base to a first bead in a first column and a single thio-modified base (or a different nucleoside or modified nucleoside monomeric unit) to a second bead in a second column and mixing the first and second beads. Next, the mixed first and second beads are split into the first and second columns, a new base is added to the separated beads in each of the first and second columns and the steps of mixing the beads, splitting the beads and adding a new base in each of the first and second columns are repeated until the library is complete. The aptamers may be converted to double-stranded aptamers using, e.g., a DNA polymerase I Klenow fragment.

Yet another embodiment of the present invention is a method for detecting nucleic acid-protein interactions by mixing a one-bead, one-ODN combinatorial library with one or more proteins and detecting the binding of the protein to one or more beads of the one-bead, one-ODN combinatorial library. The reaction is carried-out generally under conditions that permit the binding of a second protein to the protein bound to the one or more beads. Also, the sequence on the bead may be determined by isolating the bead and sequencing the unique aptamer bound to the bead, which may be done, e.g., to compare the level of protein bound to one or more of the beads a control and a test sample. The level of protein bound to the one or more beads may also be from a control and a patient sample.

Another method of the present invention is a way to identify proteins differentially expressed in a sample, by mixing a one-bead, one-ODN aptamer bead library where the sample has been labeled with a first dye and with a control labeled with a second dye under conditions that allow binding followed by sorting the bead library and comparing the relative levels of each of the first and second dyes on each bead. In this assay the differences in the level of the first or second dye are used to determine the level of binding of the sample and the control to the beads in the bead library. The beads may be sorted by a flow cytometer or even manually. For sample evaluation the present method may also include the step of isolating the one or more beads and determining the characteristics of the bound material by SELDI-MS. The first and second dyes are fluorescent dyes, e.g., cy3 and cy5. The method may also include placing the library of beads onto a substrate. Using the methods of the present invention, it is also possible to increase the amount of dyes or other chromo or fluorophores to achieve sorting of the beads in the bead library by a variable selection criteria, e.g., a low, medium and/or high signal selection criteria.

According to one embodiment of the present invention, the modified nucleotide aptamer can contain a phosphoromonothioate or phosphorodithioate ("phosphorothioates") and can be selected from the group consisting of dATP($\alpha$S), dTTP($\alpha$S), dCTP($\alpha$S) and dGTP($\alpha$S). In another embodiment of the present invention, no more than three adjacent phosphate sites of the modified nucleotide aptamer are replaced with phosphorothioate groups. In yet another embodiment of the present invention, at least a portion of non-adjacent dA, dC, dG, or dT phosphate sites of the modified nucleotide aptamer are replaced with phosphorothioate groups. In yet another embodiment of the present invention, all of the non-adjacent dA, dC, dG, or dT phosphate sites of the modified nucleotide aptamer are replaced with phosphorothioate groups. In yet another embodiment of the present invention, all of the non-adjacent dA, dC, dG, and dT phosphate sites of the modified nucleotide aptamer are replaced with phosphorothioate groups. In still another embodiment of the present invention, substantially all non-adjacent phosphate sites of the modified nucleotide aptamer are replaced with phosphorothioate groups.

In accordance with another embodiment of the present invention, the target molecule or portion thereof is NF-κB. In accordance with another embodiment of the present invention, the aptamer is selected to bind NF-κB or constituents thereof and is essentially homologous to the sequences of oligonucleotides that bind NF-κB but one or more nucleotides have at least one thiophosphate or dithiophosphate group. In yet another embodiment of the present invention, the aptamer is selected to bind NF-κB or constituents thereof and wherein at least one nucleotide is an achiral thiophosphate or a dithiophosphate. In yet another embodiment of the present invention, the aptamer is selected to bind NF-κB or constituents thereof and wherein at least one nucleotide is an achiral thiophosphate or a dithiophosphate.

In yet another embodiment of the present invention, between 1 and 6 of the phosphate sites of the modified nucleotide aptamer are dithiophosphates. In another embodiment of the present invention, the modified nucleotide aptamer contains 6 dithioate linkages. In one embodiment of the invention, the detection method is selected colorimetric, chemiluminescent, fluorescent, radioactive, mass spectrometric, capacitance coupled electrical, Biacor or combinations thereof. The apparatus of the present invention may further include aptamer libraries containing multiple different but related members. In one embodiment of the present invention, the substrate for the library is selected from the group consisting of beads, membranes, glass, and combinations thereof. The substrate may even be a microarray of beads or other substrates.

In one embodiment of the present invention, an apparatus for monitoring biological interactions on the surface of the substrate, e.g., a bead library, is disclosed. The library can include a substrate, a modified nucleotide aptamer attached to the substrate, and a target protein or portion thereof. The target protein or portion thereof may be complexed with the modified nucleotide aptamer under conditions sufficient to allow complexation between the aptamer and the target protein or portion thereof. The modified nucleotide aptamer may include an oligonucleotide having a desired binding efficiency for a target protein or portion thereof.

According to one embodiment of the present invention, the modified nucleotide aptamer is selected by the steps of: attaching a first base to a bead or other substrate; synthesizing a random phosphodiester oligonucleotide combinatorial library wherein constituent oligonucleotides comprise at least a set of 5' and 3' PCR primer nucleotide sequences flanking a randomized nucleotide sequence using a split synthesis method, adding the next base, wherein at least a portion of at least one of the nucleotides in the mix is thiophosphate-modified, to form a partially thiophosphate-modified oligonucleotide combinatorial library, and repeating the steps of adding a base that is either thiophosphate-modified of a phosphodiester linked nucleotide iteratively a population of sequences is obtained.

According to one embodiment of the present invention, the steps in which any number of beads are included in a column that adds a thiophosphate-modified base is limited so that no more than three adjacent phosphate sites of the modified nucleotide aptamer are replaced with phosphorothioate groups.

The present thioaptamer methodology may also provide a library and method of use for identifying aptamers that are improvement over existing antisense or "decoy" oligonucleotides because of their stereochemical purity. Chemically synthesized phosphorothioates may be a diastereomeric mixture with $2^n$ stereoisomers with n being the number of nucleotides in the molecule. These preparations are unsuitable for use in humans because only a small fraction of the stereoisomers will have useful activity and the remaining could have potential adverse effects. In contrast, enzymatically synthesized oligonucleotides are stereochemically pure due to the chirality of polymerase active sites. Inversion of configuration is believed to proceed from $R_p$ to $S_p$ during incorporation of dNMPαS into the DNA chain. These chiral phosphormonothioates can be incorporated into the complementary strand of duplexes using polymerases and a mix of normal and at least one, but no more than three of dATP(αS), dTTP(αS), dCTP(αS) and dGTP(αS) (or NTP((αS)'s for RNA thioaptamers) as described in (Gorenstein, D. G., et al., U.S. Pat. No. 6,423,493). The present dithiophosphate aptamers are free from diastereomeric mixtures.

The present inventors have developed chemically synthesized combinatorial libraries of unmodified or modified nucleic acids and methods for using the same, to select rapidly oligonucleotides that bind to target biomolecules, e.g., proteins. The present inventors used a split synthesis methodology to create one-bead one-S—ODN and one-bead one-$S_2$—ODN libraries. Binding and selection of specific beads to the transcription factor NF-κB p50/p50 protein were demonstrated. Sequencing both the nucleic acid bases and the positions of any 3'-O-thioate/dithioate linkages was carried out by using a novel PCR-based identification tag of the selected beads. The use of a PCR-based identification tag allowed the rapid and convenient identification of S—ODNs or $S_2$—ODNs that bound to proteins. Phosphorothioate oligonucleotides (S—ODN) or phosphorodithioate oligonucleotide ($S_2$—ODNs) with sulfurs replacing one or both of the non-bridging phosphate oxygens were shown to bind to proteins more tightly than unmodified oligonucleotides, and have the potential to be used as diagnostic reagents and therapeutics.

The present invention is a one-bead, one-compound library made by using a split synthesis method to create an alternative to in vitro combinatorial selection methods. One-bead library systems have been used for organic molecules (Felder, E. R. (1999) Resins, Linkers And Reactions For Solid-Phase Synthesis Of Organic Libraries. In Miertus, S. (ed.), *In Combinatorial Chemistry and Technology, Principles, Methods and Applications*. Marcel Dekker, Inc., NY, pp. 35-51.); peptides (Lam, K. S., et al., (1991) A new type of synthetic peptide library for identifying ligand-binding activity. *Nature,* 354, 82-84; Lam, K. S., et al., (1997) The "one-bead-one-compound" combinatorial library method. *Chem. Rev.,* 97, 411-448; Lam, K. S. (1995) Synthetic peptide libraries. In Molecular Biology and Biotechnology: A Comprehensive Desk Reference. Meyer, R. A. (ed.) p. 880. VCH Publisher:NY.); and oligosaccharide libraries (Zhu, T., and Boom, G. J. (1998) A two-directional approach for the solid-phase synthesis of trisaccharide libraries. *Angew. Chem. Int. Ed.,* 37, 1898-1900.; Liang, R., et al., (1996) Parallel synthesis and screening of a solid phase carbohydrate library. *Science,* 274, 1520-1522.; Hilaire, P. M. St. and Meldal, M. (2000) Glycopeptide and oligosaccharide libraries. *Angew. Chem. Int. Ed.,* 39, 1162-1179.). The present invention is the first to demonstrate a one-bead one-oligonucleotide (one-ODN) (e.g., S—ODN, $S_2$—ODN or RNA) combinatorial library selection methodology used to identifying a specific oligonucleotide aptamer that binds to specific proteins or other molecules.

Furthermore, the present invention may use $S_2$—ODN reagents with sulfurs replacing both of the non-bridging phosphate oxygens that are isosteric and isopolar with the normal phosphorodiester and are particularly advantageous for binding and screening. Importantly, $S_2$—ODNs are achiral about the dithiophosphate center, which eliminates problems associated with diastereomeric mixtures generally obtained for the chemically synthesized S—ODN. The split synthesis approach described herein was used for the construction of S—ODN, $S_2$—ODN and RNA bead-based thioaptamer libraries. For example, specific S—ODNs and $S_2$—ODNs were identified by screening of the libraries against a transcription factor NF-κB p50 or p65 heterodimers. Sequencing of both the nucleic acid bases and the positions of any 3'-O-thioate/dithioate linkages was carried out by using a novel PCR-based identification tag of the selected beads.

The controlled thiolation methodology and the libraries made thereby are applicable to the design of specific, nuclease resistant aptamers to virtually any target, but not limited to, amino acids, peptides, polypeptides (proteins), glycoproteins, carbohydrates, nucleotides and derivatives thereof, cofactors, antibiotics, toxins, and small organic molecules including, dyes, theophylline and dopamine. The nuclease resistant aptamers may be targeted against viruses, bateria, parasites, neoplastic cells and the like. It is within the scope of this invention, that the instant thioaptamers encompass further modifications to increase stability and specificity including, for example, disulfide crosslinking. It is further contemplated and within the scope of this invention that the instant thioaptamers encompass further modifications including, for example, radiolabeling and/or conjugation with reporter groups, such as biotin or fluorescein, or other functional or detectable groups for use in in vitro and in vivo diagnostics and therapeutics.

The present invention further provides the application of this methodology to the generation of novel thiolated aptamer libraries specific for nuclear factors such as, for example, NF-IL6 and NF-κB. By taking advantage of cognate binding motifs, the library may be focused to reduce library size, while also taking into account the required diversity of ODN species. The NF-κB /Rel family of transcription factors are key mediators of immune and acute phase responses, apoptosis, cell proliferation and differentiation. The NF-κB/Rel transcription factors are also key transcriptional regulators acting on a multitude of human and pathogen genes, including HIV-1.

The present structure-based dithiophosphate and combinatorial monothiophosphate library system provides for the identification of aptamers that have high specificity, and high affinity for DNA binding proteins, for example, a single NF-κB heterodimer, in a cellular extract in a rapid, single well assay followed by, e.g., rapid sorting of the bead using a flow-cytometer calibrated to the bead size(s) used to make the library. The present invention encompasses the development of separate aptamers targeting any one of the 15 possible combinations of, e.g., 5 homo- and heterodimers of the 5 different forms of NF-κB/Rel. NF-κB/Rel proteins are not only capable of transactivation (heterodimers that include NF-κB RelA(p65), c-Rel, RelA, but also repression (homodimers of NF-κB p50 or p52).

The one-bead, one-ODN libraries of the present invention may be used to study and in treatment of the many diseases in which transcription factors play a critical role in gene activation, especially acute phase response and inflammatory response. These diseases include, but are not limited to: bacterial pathogenesis (toxic shock, sepsis), rheumatoid arthritis, Crohn's disease, generalized inflammatory bowel disease, hemorrhagic fevers, autoimmune disorders, asthma, cardio-pulmonary disease, artherosclerosis, asbestos lung diseases, Hodgkin's disease, prostate cancer, ventilator induced lung injury, general cancer, AIDS, human cutaneous T cell lymphoma, lymphoid malignancies, HTLV-1 induced adult T-cell leukemia, atherosclerosis, cytomegalovirus, herpes simplex virus, JCV, SV-40, rhinovirus, influenza, neurological disorders and lymphomas.

Single-stranded nucleic acids are also known to exhibit unique structures. The best documented single-stranded nucleic acid structures are single-stranded RNA. Single-stranded DNA can also adopt unique structures. The present invention is applicable to the selection of single-stranded phosphorothioate aptamers of either RNA or DNA. Such single-stranded aptamers are applicable to both DNA (i.e., cell surface receptors, cytokines, etc.) and non-DNA binding proteins.

It is contemplated that the present methods and procedures may be scaled-up as would be necessary for high throughput thioaptamer screening and selection. For example, 6, 12, 48, 96 and 384 well microtiter plates may be used to select pools of aptamers in the one-bead, one-ODN librart to a number of different proteins under numerous conditions, e.g., for use with in conjunction with a plate reader or even an ELISA assay.

According to one embodiment of the present invention, the one-bead, one-ODN library may be employed that discriminates among 100's or even 1000's of proteins and particularly protein.protein complexes in the cell, simultaneously. Although the rate of dissociation and equilibration may vary, the rate of dissociation and equilibration of the different complexes typically is slow relative to the assay time, which is not a problem for NF-κB/Rel.

An ODN library that includes a substrate for a library, the substrate having at least one surface. Attached to the surface of the library, is a library of one-bead, one-combinatorial library ODN beads attached to the library substrate surface, thus making a library of libraries. The substrate may be, e.g., a chip, glass, glass slide, quartz, a gold surface, a surface plasmon resonance detector, a photolithographically etched micromachined microwell chip or "Texas tongue" and the like. The substrate may even be a capacitance coupled detector or other like electromagnetic, magnetic, electrical or optical detector. In one embodiment, the ODN library or libraries is made by attaching a single base to a first set of beads in a first column and attaching a mixture of unmodified or modified nucleotides, which as used herein includes unmodified bases with modified phosphate backbone(s) (i.e., sugar phosphate analogs) to a second set of beads in a second column. Next, the first and second set of beads from the first and second columns are mixed and then again into the first and second columns. A new base or a mixture of unmodified or modified bases or phosphate backbone analogs are added to the mixed beads in each of the first and second columns. These steps are repeated until the library is complete. In the final library of libraries, each of the oligonucleotides on each bead is now a combinatorial library and each unique oligonucleotide on each bead may include unmodified or a mix of modified and unmodified nucleotides.

The present invention allows for the identification, isolation and characterization of target-specific aptamers and thioaptamers by dispersing the aptamer/thioaptamer combinatorial bead library into a 2D matrix. The system and methods of the present invention may use aptamers and/or thioaptamers to target specifically a target, e.g., a peptide, protein, nucleic acid, carbohydrate, lipid or combinations thereof. The matrix may be a solid matrix or even a thixotrophic matrix. After dispersal, the beads in the combinatorial library are identified and selected from within the matrix by matrix mapping and/or chemical manipulation of bead spots by a robotic, scanning spot-picker. Available technology, such as the Oncosis Photosis technology provides high speed optical scanning to image cells and then destroys candidate cells by laser photolysis. Unlike that technology, the present invention allows for the selection, isolation and characterization of specific aptamers and thioaptamers by detecting a signal (or lack thereof) and transferring bead molecules for subsequent manipulation and/or analysis, e.g., sequencing or characterization of the aptamer and/or the target using, e.g., mass spectrometer (MS) instrumentation.

The present inventors had developed a method and system that includes the steps of: (1) incubating the combinatorial bead library with purified, labeled protein (target) mixtures or even whole proteosomes; (2) sorting the beads by flow cytometry so as to isolate those beads which have bound to protein, utilizing luminescent and other means of detection (e.g. fluorescent dye labels, binding to a primary antibody followed by binding to a fluorescent labeled secondary antibody, FRET, chemiluminescence labels, etc.); (3) mass spectrometric (MS) detection of the protein(s) bound to a single bead; (4) amplification by polymerase chain reaction (PCR) of the thioaptamer of the protein-bound bead followed by (5) sequencing of that thioaptamer.

The method for aptamer selection of the present invention may also include the steps of; dispersing a one-aptamer, one-bead combinatorial bead library into a two-dimensional matrix; scanning for aptamer beads that generate a detectable signal from interaction between the one or more aptamer beads and a target; and picking one or more aptamer beads based on the detectable signal from within the matrix. The method may also includes the step of extracting the target from the aptamer bead and/or the step of identifying the target by mass spectrometry after liquid chromatography. The one-aptamer, one-bead combinatorial bead library may be dispered within the matrix by molecular printing, e.g., using an inkjet printer. Examples of the matrix include a gel, a polymer, a thixotropic agent, a glass or a silicon matrix. The method may also include the step of separating the target into one or more peptides prior to separation by liquid chromatography. The step of identifying the target by mass spectrometry may be preceded by the steps of extracting and separating the proteins by liquid chromatography. In one embodiment, the steps of identifying the target using mass spectrometry may be matrix assisted laser desorption ionization (MALDI) mass spectrometry.

Aptamer beads for use with the invention may be, e.g., an S—ODN library or an $S_2$—ODN library. The aptamer portion of the aptamer bead may also include a colorimetric agent or fluorophore, e.g., one or more fluorophors attached to the 5' end, the 3' end or internally within the aptamers. The aptamer may also include a complementary strand to the aptamer. In some embodiments, the aptamer may be a thioaptamer, which is an aptamer that has one or more but less than all of the linkages comprising one or more of the following: rATP($\alpha$S), rUTP($\alpha$S), rGTP($\alpha$S), rCTP($\alpha$S), rATP($\alpha S_2$), rUTP($\alpha S_2$), rGTP($\alpha S_2$), rCTP($\alpha S_2$), rATP($\alpha$S), dTTP($\alpha$S), dGTP($\alpha$S), dCTP($\alpha$S), dATP($\alpha S_2$), dTTP($\alpha S_2$), dGTP($\alpha S_2$) and dCTP($\alpha S_2$), depending on whether the aptamer is an RNA and/or DNA aptamer. The aptamer, the bead and/or the target may be labeled with an enzyme, a dye, a radioisotope, an electron dense particle, a magnetic particle, a fluorescent agent, an antibody, a magnetic particle or a chromophore. When the aptamer, bead and/or target are labeled, these may be detectable with an enzyme, a radioisotope, an electron dense particle, a magnetic particle, a fluorescent agent, an antibody, a magnetic particle or a chromophore.

The aptamer bead may be further processed to remove the target bound to the aptamer bead, e.g., when the aptamer bead is acquired by a scanning robotic head and the target is extracted from the aptamer bead in situ. In one embodiment, e.g., the aptamer bead is acquired by a scanning robotic head and the target is extracted from the aptamer bead in situ by proteolysis and transferred to the inlet of an LC-MS or an LC-MS/MS. Alternatively, the aptamer bead is acquired by a scanning robotic head and the target is extracted from the aptamer bead in situ for MALDI-MS analysis, wherein the MALDI-MS analysis is selected from the group consisting of MALDI-TOF/MS, MALDI-TOF/TOF-MS and MALDI-Q-TOF-MS. Yet other alternatives for the scanning robotic head to acquire the aptamer bead and the target may be: (1) extracted from the aptamer bead in situ for LC-MS analysis, (2) extracted from the aptamer bead in situ for MALDI-MS analysis; and/or (3) extracted from the aptamer bead in situ for MALDI-MS analysis by SELDI ionization. The aptamer bead may be further processed to remove the target bound to the aptamer bead and analyzing the target by MS, MS/MS, MALDI-TOF, MALDI-TOF-MS, direct sequencing, in some cases the MALDI ionization step may be a SELDI ionization. The aptamer bead may also be processed to remove the target bound to the aptamer bead and the target further analyzed by binding a second detectable label to the target.

To disperse the aptamer beads before or after being exposed to a target under conditions that permit binding, the same may be dispersed, printed, attached or placed into a generally two-dimensional and even three-dimensional thixotrophic agent, e.g., a polyacrylamide gel, an alkyd resin or a silica-lipid. Following dispersal and binding of the aptamer-bead to the target to form a complex, the complex is imaged and the beads selected for capture may be selected by picking the beads manually, semi-manually or non-manually. Examples of targets include, e.g., peptides, proteins, nucleic acids, carbohydrates, lipids or combinations thereof. In one example, the aptamer beads may be dispersed within the thixotropic agent by molecular printing, e.g., an ink-jet printer.

Yet another example of the present invention is a system and method for aptamer selection that includes dispersing a one-aptamer, one-bead combinatorial bead library into a two-dimensional matrix; scanning for aptamer beads that generate a detectable signal from interaction between the one or more aptamer beads and a target; and picking one or more aptamer beads based on the detectable signal from within the matrix. The one-aptamer, one-bead combinatorial bead library is dispered within the matrix by molecular printing, e.g., using an inkjet printer. The two-dimensional matrix may be, e.g., a gel, a polymer, a thixotropic agent, a glass or a silicon matrix.

The present invention also includes a system for aptamer selection in which a two-dimensional matrix is used to separate two or more aptamer beads bound to a target; a scanner that images a signal from the two or more aptamer beads bound to a target; and a spot-picker that picks one or more aptamer beads bound to a target. The spot-picker is used to transfer one or more aptamer-bead bound to a target to a chamber for further chemical manipulation, e.g., aptamer sequencing. The spot-picker may be a robotic spot picker. The two-dimensional matrix may be a gel, a polymer, a thixotropic agent, a glass or a silicon matrix. In one specific embodiment, the spot-picker transfers one or more aptamer-bead bound targets to a bead-target separator; and a conduit connected to the chamber allows transfer of the targets into a liquid chromatograph or even a liquid chromatograph and a mass spectrometer, e.g., a matrix assisted laser desorption ionization mass spectrometer.

The present invention uses a two dimensional (2D) robotic spot picker to identify a target, e.g., a protein, on an individual bead of a combinatorial bead library that had been incubated with a target to for an aptamer-bead-target complex. The subject invention may use, e.g., a combinatorial bead library/protein incubation step of the existing methodology. One advantage of the present invention is that it does not require flow cytometry to isolate those beads that have bound target protein, often a bottleneck for high-throughput analysis. Instead, the invention scans and picks target bead spots, e.g., a pre-incubated target and aptamer bead library in a polyacrylamide gel, which is then cast onto a 2D plate whose bead "spots" are then imaged, analyzed and manipulated using a robotic scanning spot picker. The target and the aptamer-beads may be pre-incubated, or the target and/or the aptamer-beads may be incubated in situ. The aptamer-beads and the target are generally distributed uniformly throughout the two-dimensional matrix or agent, e.g., a gel, a gel plate, a glass plate into, e.g., a single layer. In one example, the aptamer-beads are 20-80 microns in diameter, but may be larger or smaller depending on factors such as the necessary signal-to-noise ration, amount of sample, number of beads in an aptamer-bead library, etc.

To capture, scan, image, identify and locate the spots to be picked, software available with robotic scanners and pickers, known in the art, is used to determine the XY coordinates and intensity of each bead in the 2D gel matrix, and directs and controls the hardware for manipulation of aptamer-beads and their target. For example, a high speed optical scanner based on a positional scanning excitation source (e.g. laser, diode laser) and an emission sensor (e.g. CCD camera) may be used to create a 2D image/map of candidate beads. Examples of instruments for use with the present invention include commercially available robotic spot pickers, e.g., a Bruker Daltonics Proteineer spII spot-picker (Bruker Daltonics website). Such spot pickers may be operated in conjunction with a 2D matrix, e.g., an polyacrylamide electrophoretic gel, performing 2D gel imaging, detection of protein spots of the gel, software selection, directing the robotic head to cut out ("core") a relevant spot (either automatically or based on manual review of the image map) and transfer of the spot(s) to a sample array for MS analysis. An example of a 2D imaging system is available commercially from Oncosis (Oncosis website), which uses "Photosis" technology (WO 98/42356, 1998; WO 01/40454, 2001). The Oncosis system is capable of high speed laser-based optical scanning to image a 2D matrix of cells embedded in a polymeric matrix, however, the system then re-addresses and destroys cells that are not of interest via high intensity laser photolysis.

The following are general requirements of a coring mechanism for use with the robotic head of the spot picker for use with the present invention. The coring mechanism of the robotic head of the spot picker, will generally transfer a candidate bead from the cast gel matrix to, e.g., a mass spectrometer inlet. To do so it will generally capture only one bead at a time. As such, the coring mechanism will generally be designed to have a diameter less than that of two beads. To introduce a bead into the interior of a cylinder, e.g., a needle, the inner diameter of the cylinder has to be greater than that of one bead. However, if a bead or plug is not to be fully captured within the cylinder, then the item may be held outside the tip of the cylinder using, e.g., application of a vacuum to the other end of the cylinder to cause a vacuum within the cylinder. Thus, there is a suitable range between one bead diameter and less than two bead diameters.

For example, if the beads are 60 micron diameter, the coring mechanism must have a diameter between 80-100 microns. If this requirement is not met, the possibility exists that the coring mechanism will transfer more than one bead in a single "core." The "bystander" bead(s) transferred may also be candidate beads (also bind target protein and thus have appropriate fluorescent signature) or may be non-candidates (do not bind protein, do not have fluorescent signature). Where the single "core" contains "bystander" candidate beads, the mass spectrum of the multiple proteins (or peptide digests if on-gel digestion is used) will be difficult to interpret. Where the single "core" contains "bystander" non-candidate beads, the identification of the binding thioaptamer of the candidate bead will be difficult.

BRIEF DESCRIPTION OF THE DRAWINGS

For a more complete understanding of the features and advantages of the present invention, reference is now made to the detailed description of the invention along with the accompanying figures and in which:

FIG. 6 shows the identification of thioaptamer sequences selected for highest binding to NF-κB using either direct flurorescence labeling of protein or sandwich assay using "one bead PCR" method);

DETAILED DESCRIPTION OF THE INVENTION

Figure 1:
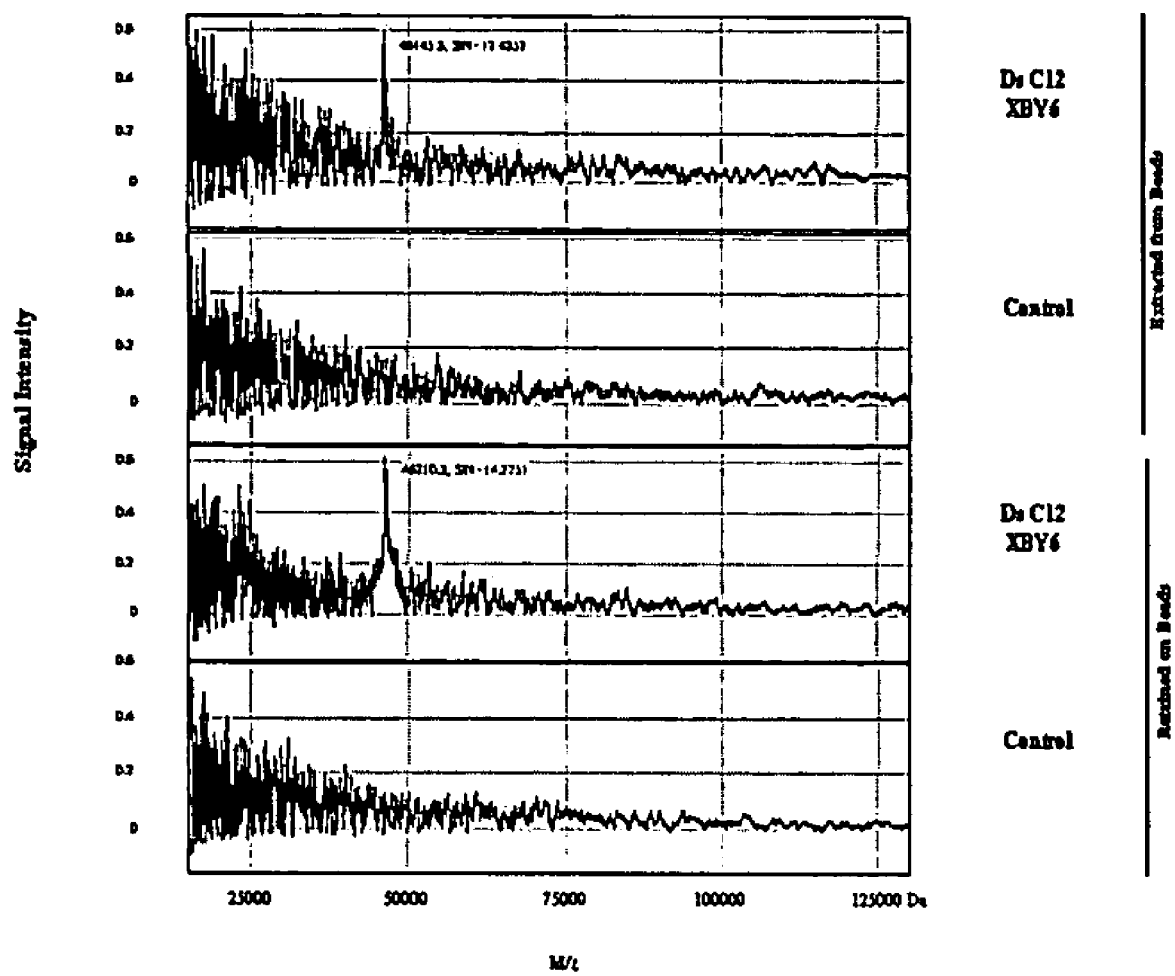
FIG. 1 shows a MALDI (SELDI) identification of proteins bound to aptamer beads by either direct laser desorption and MALDI MS detection of p50 NF-κB or dissociation of protein from beads and MALDI detection.
Figure 2:
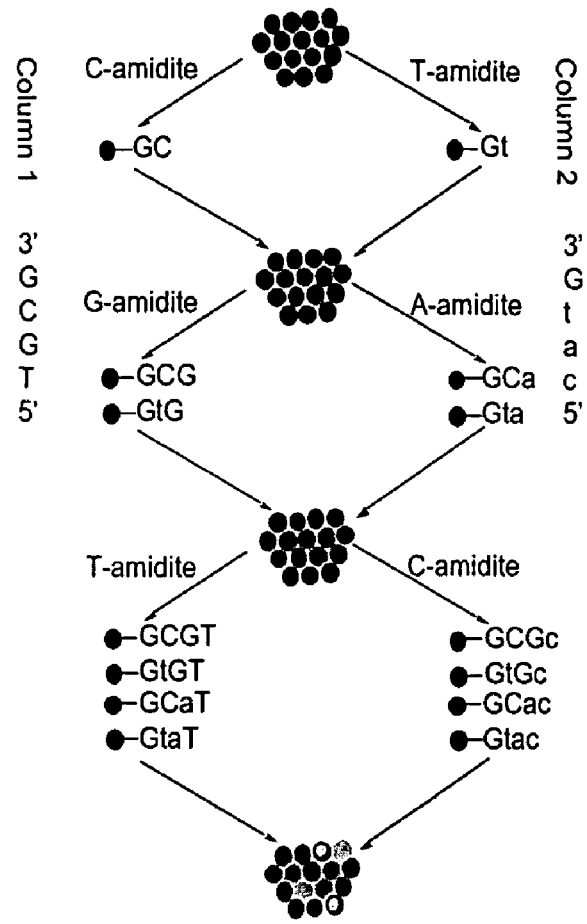
FIG. 2 is a schematic diagram for split synthesis of thioaptamer bead combinatorial libraries or library of libraries.
Figure 3:
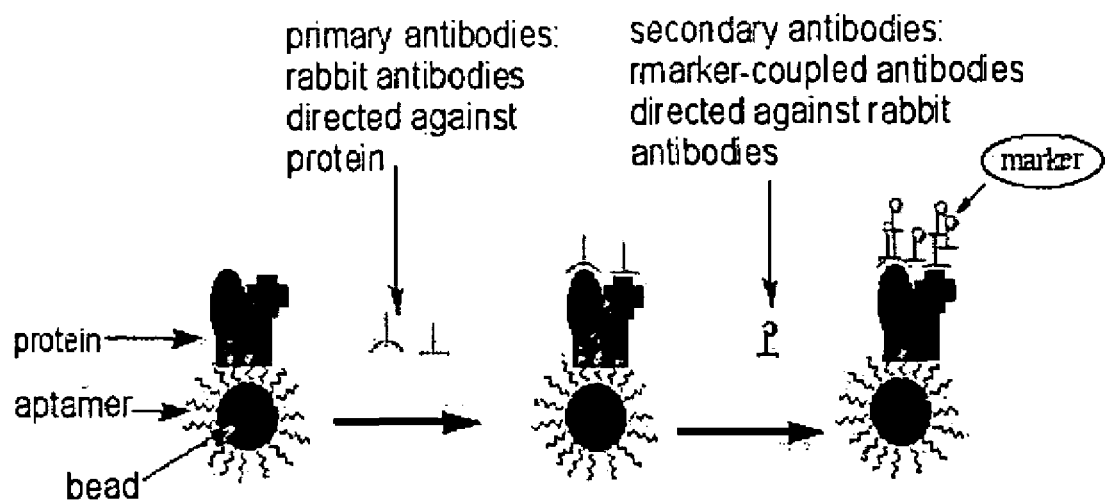
FIG. 3 shows a fluorigenic sandwich assay for identifying proteins bound to thioaptamer beads.
Figure 4:
FIG. 4 shows a sandwich assay demonstrating two color imaging of either p50 or p65 forms of NF-κB bound to aptamer beads.
Figure 5:
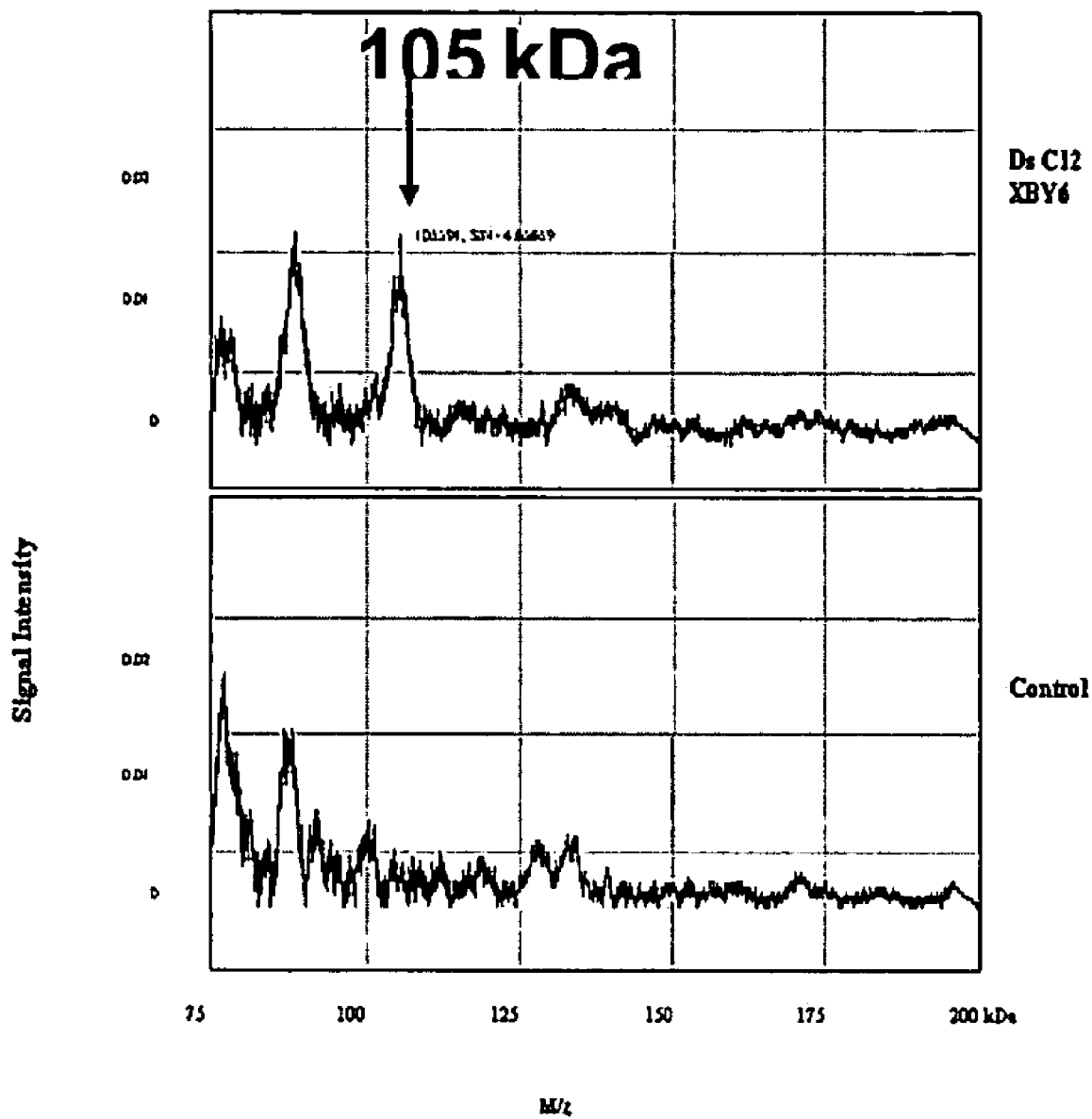
FIG. 5 shows the SELDI (MALDI) identification of a 105 kDa protein in nuclear extracts form macrophages activated by LPS, bound to thioaptamer surfaces (ProteinChip)
Figure 7:
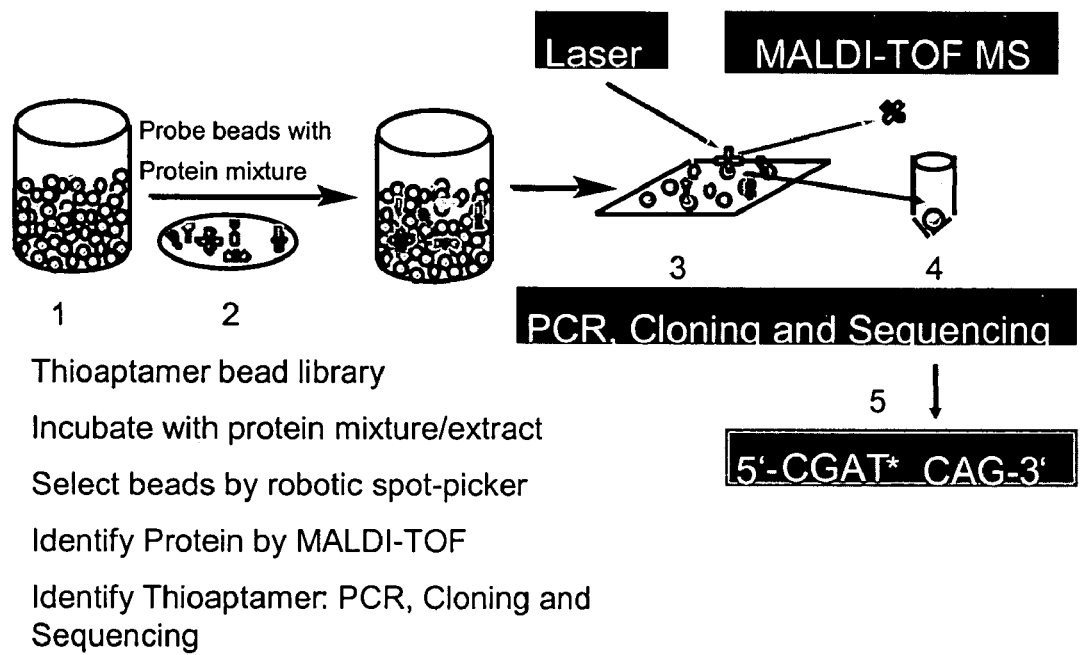
FIG. 7 is a drawing that summarized a selection scheme of the subject invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, "synthesizing" of a random combinatorial library refers to chemical methods known in the art of generating a desired sequence of nucleotides including where the desired sequence is random. Typically in the art, such sequences are produced in automated DNA synthesizers programmed to the desired sequence. Such programming can include combinations of defined sequences and random nucleotides.

"Random combinatorial oligonucleotide library" means a large number of oligonucleotides of different sequence where the insertion of a given base at given place in the sequence is random. "PCR primer nucleotide sequence"

refers to a defined sequence of nucleotides forming an oligonucleotide which is used to anneal to a homologous or closely related sequence in order form the double strand required to initiate elongation using a polymerase enzyme. "Amplifying" means duplicating a sequence one or more times. Relative to a library, amplifying refers to en masse duplication of at least a majority of individual members of the library.

As used herein, "thiophosphate" or "phosphorothioate" are used interchangeably to refer analogues of DNA or RNA having sulphur in place of one or more of the non-bridging oxygens bound to the phosphorus. Monothiophosphates or phosphoromonothioates [$\alpha$S] have only one sulfur and are thus chiral around the phosphorus center. Dithiophosphates are substituted at both oxygens and are thus achiral. Phosphoromonothioate nucleotides are commercially available or can be synthesized by several different methods known in the art. Chemistry for synthesis of the phosphorodithioates has been developed by one of the present inventors as set forth in U.S. Pat. No. 5,218,088 (issued to Gorenstein, D. G. and Farschtschi, N., Jun. 8, 1993 for a Process for Preparing Dithiophosphate Oligonucleotide Analogs via Nucleoside Thiophosphoramidite Intermediates), relevant portions incorporated herein by reference.

"Modified" is used herein to describe oligonucleotides or libraries in which one or more of the four constituent nucleotide bases of an oligonucleotide are analogues or esters of nucleotides normally comprising DNA or RNA backbones and wherein such modification confers increased nuclease resistance. Thiophosphate nucleotides are an example of modified nucleotides. "Phosphodiester oligonucleotide" means a chemically normal (unmodified) RNA or DNA oligonucleotide. Amplifying "enzymatically" refers to duplication of the oligonucleotide using a nucleotide polymerase enzyme such as DNA or RNA polymerase. Where amplification employs repetitive cycles of duplication such as using the "polymerase chain reaction", the polymerase may be, e.g., a heat stable polymerase, e.g., of *Thermus aquaticus* or other such polymerases, whether heat stable or not.

"Contacting" in the context of target selection means incubating a oligonucleotide library with target molecules. "Target molecule" means any molecule to which specific aptamer selection is desired. "Essentially homologous" means containing at least either the identified sequence or the identified sequence with one nucleotide substitution. "Isolating" in the context of target selection means separation of oligonucleotide/target complexes, preferably DNA/protein complexes, under conditions in which weak binding oligonucleotides are eliminated.

By "split synthesis" it is meant that each unique member of the combinatorial library is attached to a separate support bead on a two column DNA synthesizer, a different thiophosphoramidite or phosphoramidite is first added onto both identical supports (at the appropriate sequence position) on each column. After the normal cycle of oxidation (or sulfurization) and blocking (which introduces the phosphate, monothiophosphate or dithiophosphate linkage at this position), the support beads are removed from the columns, mixed together and the mixture reintroduced into both columns. Synthesis may proceed with further iterations of mixing or with distinct nucleotide addition.

Aptamers may be defined as nucleic acid molecules that have been selected from random or unmodified oligonucleotides ("ODN") libraries by their ability to bind to specific targets or "ligands." An iterative process of in vitro selection may be used to enrich the library for species with high affinity to the target. The iterative process involves repetitive cycles of incubation of the library with a desired target, separation of free oligonucleotides from those bound to the target and amplification of the bound ODN subset using the polymerase chain reaction ("PCR"). The penultimate result is a sub-population of sequences having high affinity for the target. The sub-population may then be subcloned to sample and preserve the selected DNA sequences. These "lead compounds" are studied in further detail to elucidate the mechanism of interaction with the target.

The present inventors recognized that it is not possible to simply substitute thiophosphates in a sequence that was selected for binding with a normal phosphate ester backbone oligonucleotide. Simple substitution was not practicable because the thiophosphates can significantly decrease (or increase) the specificity and/or affinity of the selected ligand for the target. It was also recognized that thiosubstitution leads to a dramatic change in the structure of the aptamer and hence alters its overall binding affinity. The sequences that were thioselected according to the present methodology, using as examples of DNA binding proteins both NF-IL6 and NF-$\kappa$B, were different from those obtained by normal phosphate ester combinatorial selection.

The present invention takes advantage of the "stickiness" of thio- and dithio-phosphate ODN agents to enhance the affinity and specificity to a target molecule. In a significant improvement over existing technology, the method of selection concurrently controls and optimizes the total number of thiolated phosphates to decrease non-specific binding to non-target proteins and to enhance only the specific favorable interactions with the target. The present invention permits control over phosphates that are to be thio-substituted in a specific DNA sequence, thereby permitting the selective development of aptamers that have the combined attributes of affinity, specificity and nuclease resistance.

In one embodiment of the present invention, a method of post-selection aptamer modification is provided in which the therapeutic potential of the aptamer is improved by selective substitution of modified nucleotides into the aptamer oligonucleotide sequence. An isolated and purified target binding aptamer is identified and the nucleotide base sequence determined. Modified achiral nucleotides are substituted for one or more selected nucleotides in the sequence. In one embodiment, the substitution is obtained by chemical synthesis using dithiophosphate nucleotides. The resulting aptamers have the same nucleotide base sequence as the original aptamer but, by virtue of the inclusion of modified nucleotides into selected locations in the sequences, improved nuclease resistance and affinity is obtained.

EXAMPLE 1

S—ODN, $S_2$—ODN and Monothio-RNA Split and Pool Synthesis

A split and pool synthesis combinatorial chemistry method was developed for creating combinatorial S—ODN, $S_2$—ODN and monothio-RNA libraries (and readily extended to unmodified ODNs-whether single strand or duplex). In this procedure each unique member of the combinatorial library was attached to a separate support bead. Targets that bind tightly to only a few of the potentially millions of different support beads can be selected by binding the targets to the beads and then identifying which beads have bound target by staining and imaging techniques. The methodology of the present invention allowed the rapid screening and identification of aptamers that bind to proteins such as NF-κB using a novel PCR-based identification tag of the selected bead.

The dA, dG, dC and dT phosphoramidites were purchased from Applied Biosystems (Palo Alto, Calif.) or Glen Research (Sterling, Va.). The Beaucage reagent (3H-1,2-Benzodithiol-3-one 1,1-dioxide) was from Glen Research. The Taq polymerase kits were from Applied Biosystems. The TA Cloning kit was from Invitrogen. The Klenow DNA polymerase I was from Promega. Polystyrene beads (60-70 μm) with non-cleavable hexaethyleneglycol linkers with a loading of 36 μmol/g were from ChemGenes Corp (Ashland, Mass.). The Alexa Fluor 488 dye was from Molecular Probes, Inc (Eugene, Oreg.). The dA, dG, dC and dT thiophosphoramidites were synthesized as previous described (Yang, X-B., Fennewald, S., Luxon, B. A., Aronson, J., Herzog, N. and Gorenstein, D.G., "Aptamers containing thymidine 3'-O-phosphorodithioates: Synthesis and binding to Nuclear Factor-κB, *J. Bioorganic and Medicinal Chemistry*, 9, 3357-3362 (1999) and refs therein). The ODNs and S—ODNs used in the study were synthesized on a 1-μmol scale on an Expedite 8909 System (Applied Biosystems) DNA Synthesizer.

Synthesis of S—ODN and $S_2$—ODN libraries. Standard phosphoramidite and thiophosphoramidite chemistry was used for the S—ODN and $S_2$—ODN libraries, respectively. The libraries were prepared on a 1 μmole scale of polystyrene beads. The downstream and upstream primers, 5'-GGATCCGGTGGTCTG-3' (SEQ ID NO:1) and 5'-CCTACTCGCGAATTC-3' (SEQ ID NO:2) were synthesized in parallel on a two-column DNA synthesizer (Expedite 8909, Applied Biosystems). Following the 5'-primer, the sequences programmed on the synthesizer for the combinatorial S—ODN library were 5'-*CA*GT*TG*AG*GG*GA*CT*TT*CC*CA*GG*C-3' (SEQ ID NO:3) on column 1 and 5'-*cC*tG*cA*cA*tC*tC*aG*gA*tG*aC*tT*t-3' (SEQ ID NO:4) on column 2. The sequences programmed for the combinatorial $S_2$—ODN library were 5'-ATGT*AGCC*A*GCTAGT*CTG*TCAG-3' (SEQ ID NO:5) on column 1 and 5'-CGCC*cAGT*g*aAGGTG*gaA*CCCC-3' (SEQ ID NO:6) on column 2. The 3'-primer sequence completed the 52-mer programmed on the synthesizer.

A "split and pool" occurred at each position indicated by an asterisk in order to synthesize the combinatorial region for the S—ODN and $S_2$—ODN. The lower case letter indicates a 3'-thioate linkage, the upper case letter indicates a 3'-phosphate linkage, while the lower case bold letter indicates a 3'-dithioate linkage. The coupling yield was typically upwards of 99% as determined by the dimethoxytrityl cation assay. Sulfurization chemistry used the Beaucage reagent. The fully protected S—ODN or $S_2$—ODN combinatorial libraries with the non-cleavable linker beads were treated with concentrated ammonia at 37° C. for 21 hours to remove the protecting groups while allowing the ODN to remain attached to the beads. The S—ODN or $S_2$—ODN bead-based single-strand (ss) DNA library was washed with double distilled water. The ssDNA library (typically 1-3 mg of support beads) was converted to a double-strand (ds) DNA by Klenow DNA polymerase I reaction in the presence of DNA polymerase buffer, dNTP mixture and reverse primer according to the manufacture. The dsDNA library was washed twice with phosphate-buffered saline (PBS).

Briefly, a solid-phase synthesis of a one-bead one-S/$S_2$—ODN library is as follows. In a first cycle, in column 1, a phosphoramidite dC was used to form a dinucleotide phosphotriester dGC via a phosphotriester linkage, in column 2, a phosphoramidite T was used to form a dinucleotide thiophosphotriester dGt via a phosphothiotriester linkage. Upon pooling, the end products are a mixture of two kinds of bead-bound dinucleotides include phosphorotriester and phosphothiotriester. After splitting and pooling through three such cycles the eight ($2^3$) possible ODN and/or S—ODN tetraoligonucleotides are represented on separate beads. A lowercase letter denotes a 3'-thioate, while an uppercase letter denotes a 3'-phosphate. The $S_2$—ODN library was generated by replacing the phosphoramidite with a thiophosphoramidite globally in column 2. The sulfurization step immediately followed the thiophosphoramidite coupling step.

Labeling NF-κB p50/50 protein with Alexa Fluor 488. To 0.5 ml of p50/50 protein (0.215 mg/ml, expressed and purified (King, D., et al. (2002) Combinatorial selection and binding of phosphorothioate aptamers targeting human NF-κB RelA (p65) and p50. *Biochemistry*, 41, 9696-9706, relevant portions incorporated herein by reference) in PBS containing 30% glycerol was added 50 μl of 1 M bicarbonate. The protein was transferred to a vial of reactive Alexa Fluor 488 dye and stirred at room temperature for 1 hr. Fluorescently labeled protein was purified according to procedures from Molecule Probes, Inc. The labeled protein was stored at 4° C. in the dark.

Alexa Fluor 488 labeled NF-κB p50/p50 binding to beads, selection of beads. A portion of the ds S—ODN or $S_2$—ODN library (ca. 3.0 mg of the beads) was suspended in 300 μl of blocking buffer (PBS containing 0.05% Tween-20) and incubated at room temperature for 1 hr in a microcentrifuge tube. The beads were washed with 300 μl of PBS and pelleted by centrifugation. The beads were suspended in 300 μl of Alexa Fluor 488 labeled NF-κB p50/p50 (0.07 μg/μl) at room temperature for two hrs and then washed with blocking buffer (2×300 μl) and PBS (2×300 μl). A portion of the beads were transferred to a slide and viewed under fluorescent microscope. Individual beads with the highest fluorescence intensity were removed by a micropipette attached to a micromanipulator, sorted into PCR microcentrifuge tubes and washed with 8M urea (pH 7.2) to remove the bound protein.

One-bead one-PCR amplification and sequencing of PCR product. A selected single bead was mixed with the following PCR components: 6 μl of 25 mM $MgCl_2$ (8 μl for 15, 10 and 8 mer primers), 0.5 μl of Taq polymerase (5 units/μl), 1 μl of 8 mM dNTP, and 10 μl of PCR buffer and 1 μl of 40 mM primers. The PCR was run on a GeneAmp PCR system 2400 (Perkin Elmer). The PCR reaction mixtures were thermal cycled using the following scheme for amplification: 94° C. for 5 min (1 cycle); 94° C. for 2 min, 55° C. for 2 min (35° C. for 10 and 8mer primers), 72° C. for 2 min (35 cycles); and 72° C. for 7 min (1 cycle). The PCR products were analyzed on a 15% native polyacrylamide gel. The PCR product was cloned using the TA Cloning procedure (Invitrogen) and sequenced on an ABI Prism 310 Genetic Analyzer (Applied Biosystems).

One-bead one-oligonucleotide libraries. A primary consideration for designing a one-bead, one-ODN library using phosphoramidite chemistry was defining suitable bead linker chemistry where the ODNs can be synthesized and yet remain attached covalently to the beads after full deprotection. Additional considerations include development of the split synthesis method for construction of the ODN library, screening bead-based ODN libraries in aqueous media for one-bead binding assays and sequencing of the ODN bound on the individual bead. Although long-chain alkylamine controlled-pore glass (LCA-CPG) (Pierce Chemical Co., Rockport, Ill.) has been used for many years for efficient ODN synthesis, LCA-CPG may not always be suitable for generation of one-bead, one-ODN libraries. The size, homogeneity and the swelling of CPG are factors to consider when selecting a chemistry for a one-bead, one-ODN library. For example, one disadvantage of the CPG linker chemistry available currently is that ODNs are cleaved from the solid support during the ammonia deprotection step. An advance in solid support chemistry has been the ability to synthesize ODNs on more uniform polystyrene beads. Importantly, using chemistry with a non-cleavable hexaethyleneglycol linker attaching the first phosphoramidite (ChemGenes Corp.), the synthesized ODNs are still attached covalently to the beads after full base and phosphate ester deprotection. In this procedure each unique ODN chemical entity in the combinatorial library is attached to a separate support bead. Selection of a bead-based ODN combinatorial library can then be carried out by binding the bead library of ODNs to a target protein under high stringency conditions where only a few beads show binding.

Following the in vitro combinatorial selection method for identification of selected ODN sequences, the ODN sequence on the selected beads may be identified. For example, 5' and 3' fixed ODN primer sequences flanking the combinatorial library segment of the ODN may be used to aid in the identification. Fixed primer regions allow PCR amplification of the sequence as well as Klenow extension of the ssDNA attached covalently to produce a combinatorial library of dsODN attached to the beads.

Primers design for one-bead one-ODN. Initially, a template ODN with a predetermined 14mer sequence region flanked by two 18mer primers on the beads were synthesized (ODN 1 in Table 1). Its ability to support one-bead one-PCR amplification was studied for several individual beads. The PCR product was cloned using the TA Cloning procedure and sequenced on an ABI Prism 310 Genetic Analyzer. The desired sequence was confirmed. Although 18mer or longer primers are generally used in PCR amplification, shorter primers are attractive since the size of the ODN is limited by the synthesis yields for long ODNs.

TABLE 1

ODNs on beads and primers

ODNs on beads used as templates
ODN1:
5'-ATGCCTACTCGCGAATTC-CCAGGAGATTCCAC-   (SEQ ID
GGATCCGGTGGTCTGTTC-Bead                 NO:7)

ODN2:
5'-CCTACTCGCGAATTC-AGTTGAGGGGACTTTCCCAGGC-  (SEQ ID
GGATCCGGTGGTCTG-Bead                        NO:8)

Primers

Upstream primers         Downstream primers
(SEQ ID NO:9)            (SEQ ID NO:10)

18mer:
5'-ATGCCTACTCGCGAATTC-3'    5'-GAACAGACCACCGGATCC-3'

15mer:
5'-CCTACTCGCGAATTC-3'       5'-CAGACCACCGGATCC-3'

10mer:
5'-CCTACTCGCG-3'            5'-CAGACCACCG-3'

8mer:
5'-CCTACTCG-3'              5'-CAGACCAC-3

Note: the 15-mer, 10-mer and 8-mers are nested oligos of: SEQ ID NO:9 and SEQ ID NO:10, respectively.

Consequently, longer combinatorial sequence libraries would be possible with shorter primer sequences; in addition, shorter primer sections will reduce non-specific binding of target proteins to the ODN bead library. To study the primer length requirement for one-bead one-PCR amplification, a series of primers with varying lengths (8mer, 10mer and 15mer; see Table 1) were designed and synthesized to hybridize to the 52mer template ODN containing both 5' and 3' primer regions (ODN 2 in Table 1) on the support beads. The PCR products of these primers were monitored by 15% polyacrylamide gel electrophoresis. The PCR conditions were optimized for each pair of primers of varying length. No detectable band was observed with the 8mer primers, even at the highest concentration tested (data not shown). A weak band was detected with the 10mer primers, while a strong band was observed with 15mer primers (data not shown). The fidelity in the Taq polymerase amplification yielding the ODN products was confirmed by cloning and sequencing (data not shown). These results suggest that ODNs with primer lengths of 10 nt or greater are required for efficient PCR amplification. In this study, 15mer primers were selected for the following studies.

Generation of a self-encoded $S/S_2$—ODN library. To introduction many copies of a single, chemically pure S—ODN or $S_2$—ODN onto each bead, a "mix and separate" split synthesis method was used. A two-column DNA synthesizer was used for constructing the library. The normal phosphate backbone linkages were generated using standard phosphoramidite monomers via oxidation in column 1, while the phosphorothioate or phosphorodithioate linkages were synthesized using standard phosphoramidite or thiophosphoramidite monomers via sulfurization in column 2, respectively. Two sequences of the same length are programmed for each column and are designed such that the bases are different at every equal position not only for diversifying base compositions but also for coding a phosphate, phosphorothioate or phosphorodithioate linkage. Thus, on an Expedite 8909 DNA synthesizer with dual columns, for example, onto column 1 a phosphoramidite (for example: dC) is coupled to the bead and after completion of oxidation, the resulting product is nucleotide (dC) with a phosphotriester linkage. On column 2, a nucleoside phosphorothioate or phosphorodithioate is introduced with a different base (dT for example). The support beads from the two columns are mixed and resplit and in the second cycle, additional phosphoramidites or thiophosphoramidites are introduced, followed by oxidation and sulfurization reactions individually in columns 1 and 2.

After additional coupling steps and after final split/pool synthesis is completed, the end products comprise a combinatorial library of ODNs with varying thioate/dithioate or normal phosphate ester linkages at varying positions along the ODN strand attached to the support. Each bead contains a single chemical entity with a specified backbone modification that is identified by the base. In the above example, any dC at position 1 of the sequence will be a 3'-phosphate while a dT at position 1 would indicate that it contains a 3'-thiophosphate. This scheme was applied to synthesize a library of 4096 ($2^{12}$) one-bead, one-S—ODN. This library included a 22-nucleotide combinatorial sequence (12 split/pool steps) flanked by 15 nucleotide defined primer regions at the 5' and 3' ends (see Table 1). The 3' ends of the sequences were attached to the polystyrene beads. As noted above, the defined primer sequences were incorporated to allow PCR amplification and identification of the ODN sequence on the selected beads. Thus, the downstream primers were first automatically synthesized in parallel on the two columns. The S—ODN sequences of the combinatorial 22-mer segment on each column were programmed for each column and were generated by introducing a phosphorothioate linkage on every other base in column 2, following the "split and pool" approach. The identical upstream primer sequences were then completed on both columns. As described below, a smaller $S_2$—ODN library was created in similar fashion.

Selection and sequencing of the S—ODN beads. Binding of the transcription factor NF-κB p50/p50 homodimer and selection of specific beads was demonstrated by first converting the single-stranded S—ODN to dsDNA since the NF-κB transcription factor binds to DNA duplexes. The single-stranded 52-mer S—ODN combinatorial library (typically 1-3 mg of beads) was converted to dsDNA by Klenow DNA polymerase I reaction in the presence of DNA polymerase buffer, dNTP mixture and reverse primer. Therefore, one strand of the duplex potentially contained thiophosphate backbone substitutions in the combinatorial library segment and the other complementary strand included an unmodified phosphate backbone ODN. A duplex DNA library in which both strands contain S—ODN modifications could also be generated using a Klenow reaction with no more than three dNTP(α)S. Because the S—ODN strand attached to the support was chemically synthesized using phosphoramidite chemistry, each thiophosphate is a mixture of $R_p$ and $S_p$ stereoisomers. The beads were suspended in a diluted solution of NF-κB p50/p50 homodimer labeled with the Alexa Fluor 488 dye at room temperature for 2 hrs.

Five positive beads from the S—ODN library were selected. Each individual bead was washed thoroughly with urea to remove the protein and was directly used for the "one-bead, one-PCR" amplification using the 5' and 3' end primers described above. The PCR product was cloned and sequenced. Table 2 lists four of the S—ODN sequences obtained.

tion is only possible for thiophosphate substituted ODNs with limited P-chirality. To demonstrate how the present invention may overcome this limitation, a small one-bead, one-$S_2$—ODN library was synthesized consisting of a pool of 32 ($2^5$) sequences to allow further optimization of in vitro or bead-based S—ODN selected sequences. Chemical synthesis of $S_2$—ODN avoids problems created by a mixture of diastereoisomers of chemically synthesized S—ODN. The random region (5'-CGCCcAGTgaAGGTGgaACCCC-3') (SEQ ID NO:28) in column 2 was identified as a S—ODN sequence derived from an in vitro combinatorial selection methodology that binds the NF-κB p50/p50 protein with high affinity (<20 nM) (All lower case letters indicate enzymatically synthesized chiral 3'-thioate linkages). The programmed combinatorial region sequence (5'-ATGTAGC-CAGCTAGTCTGTCAG-3')(SEQ ID NO:19) in column 1 was designed such that the bases at each 3'-dithioate position were different from the bases in column 2 at each equal position further allowing base sequence to identify backbone substitution. Thiophosphoramidite chemistry with sulfurization was used to generate 3'-dithioate linkages. Only the previous 3'-monothioate linkages were replaced with 3'-dithioate linkages. The "split and pool" step followed most of the dithioate modifications. $S_2$—ODNs by selecting beads binding fluorescently labeled NF-κB p50/p50 homodimer were also identified, followed by PCR amplification of 5 individually selected $S_2$—ODN beads and cloning and sequencing of the PCR products. The sequences are also listed in Table 2.

The nucleic acid "aptamers" previously selected by incubating the target (protein, nucleic acid or small molecule) with the combinatorial library are then separated. The bound fractions were then amplified using PCR and subsequently

TABLE 2

S-ODNs/$S_2$-ODNs sequences identified from an NF-κB p50/p50 protein screen[a]

S-ODN selection

| Automated sequence | | Deduced S/$S_2$-ODN sequence | |
|---|---|---|---|
| CTGTGAGTCGACTGATGACGGT | (SEQ ID NOS:11-14) | CtGTGAGtCGACTgAtGaCGGt | (SEQ ID NOS:15-18) |
| AGTTGAGTCGAAGGACCCATTT | | AGTTGAGtCGAaGgACCCAtTt | |
| CGTCAAGTCTCAGTTCCCATTT | | CGTcAAGtCtCaGTTCCCAtTt | |
| AGTCAAGTCGAAGTTCCACGGT | | AGTcAAGtCGAaGTTCCaCGGt | |

$S_2$-ODN selection

| ATGTAGCCAGCTAGTCTGTCAG | (SEQ ID NOS:19-23) | ATGTAGCCAGCTAGTCTGTCAG[b] | (SEQ ID NOS:24-28) |
| CGCCAGCCAAAGGTGCTGTCAG | | CGCCAGCCaaGGTGCTGTCAG | |
| CGCCCAGTGGCTAGTGAACCCC | | CGCCcAGTggCTAGTgaACCCC | |
| ATGTAGCCGAAGGTGGAACCCC | | ATGTAGCCgaAGGTggaACCCC | |
| CGCCAGCCGAAGGTGGAACCCC | | CGCCAGCCgaAGGTggaACCCC | |

[a]The lower case letter indicates a 3'-thioate linkage. The lower case bold letter indicates a 3'-dithioate linkage.
[b]No 3'-dithioate linkages are present in this strand.

Binding and Selection of combinatorial library of $S_2$—ODN beads. $S_2$—ODNs generally bind even more tightly to proteins than unsubstituted or S—ODN analogues. Thus, it is significant that this S—ODN bead-based combinatorial selection method may be applied to dithiophosphate backbone substitutions, since in vitro combinatorial selecreincubated with the target in a second round of screening. These iterations are repeated (often 10-20 cycles) until the library is enhanced for sequences with high affinity for the target. Aptamers selected from combinatorial RNA and DNA libraries have generally had normal phosphate ester backbones, and so would generally be unsuitable as drugs or diagnostics agents that are exposed to serum or cell supernatants because of their nuclease susceptibility. Rapid degradation of natural ODNs used as antisense agents or aptamers by nucleases in serum or cells necessitates chemical modification of the ODNs.

Among a large variety of modifications, S—ODN and $S_2$—ODN modifications render the agents more nuclease resistant. The first antisense therapeutic drug uses a modified S—ODN (CIBA Vision, A Novartis Company). The $S_2$—ODNs also show significant promise, however, the effect of substitution of more nuclease-resistant thiophosphates cannot be predicted, since the sulfur substitution can lead to significantly decreased (or increased) binding to a specific protein (Milligan, J. F. and Uhlenbeck, O. C. (1989) Determination of RNA-protein contacts using thiophosphate substitutions. *Biochemistry*, 28, 2849-2290.; and Yang, X. unpublished results) as well as structural perturbations and thus it is not possible to predict the effect of backbone substitution on a combinatorially selected aptamer. Thus, if at all possible, selection should be carried out simultaneously for phosphate ester backbone substitution as well as the base sequence. Recently, an in vitro combinatorial selection of thioaptamers from random or high-sequence-diversity libraries based on their tight binding to the target (e.g. a protein or nucleic acid) of interest was demonstrated by one or more of the present inventors.

Oligonucleotides possessing high fractional substitutions of monothio/dithioate internucleotide linkages appear to be "stickier" towards proteins than normal phosphate esters, and therefore thioaptamers with complete thiophosphate backbone substitutions appear to lose much of their specificity. This increased affinity is partly due to the fact that the thioate groups only poorly coordinate hard cations such as sodium ions, and thus the thioaptamers serve as "bare" anions and don't require any energy to strip away the neutralizing cations to bind to proteins. This observation of the increased affinity is of great importance to modified-ODN design as proteins recognize DNA at both the bases and phosphate esters. In previous studies, it was demonstrated that binding of $S_2$—ODNs to a protein target requires only a limited number of phosphorodithioate linkages in a specific ODN sequence to achieve very high affinities (Gorenstein, D. G., et al., U.S. Pat. No. 6,423,493, relvant portions incorporated herein by reference).

These results demonstrate that a split and pool synthesis may be used to develop S—ODN, $S_2$—ODN and RNA libraries (which may also include unmodified ODNs-whether single strand or duplex). In this procedure each unique member of the combinatorial library was attached to a separate support bead. Targets that bind tightly to only a few of the potentially millions of different support beads were selected by binding the targets to the beads and then identifying which beads have bound target by staining and imaging techniques. The methodology of the present invention allowed the rapid screening and identification of aptamers that bind to proteins, e.g., NF-κB, using a novel PCR-based identification tag of the selected bead.

These results demonstrate that the methodology can be applied to other backbone or base modifications that are compatible with templates containing these modifications. It is important that not only the S—ODNs but even the $S_2$—ODNs are capable of acting as templates recognized by DNA polymerases for PCR amplification of selected $S_2$—ODN beads. This demonstrates that nucleic acid analogues with phosphorodithioate linkages can be used as a template in the nucleotidyltransferase reaction catalyzed by DNA polymerases. Likewise, polyamide nucleic acid (PNA) lacking the phosphate backbone may be recognized as a template for the polymerase reaction.

In vitro selection of combinatorial libraries of $S_2$—ODNs is not possible because dNTP ($\alpha S_2$) is not a substrate for polymerases. The split synthesis, bead-based $S_2$—ODN library selection method of the present invention is the only method and/or library for identifying both optimal number and location of dithioate substitutions as well as base sequences for these $S_2$—ODN aptamers. Additionally, even for the thioate library selection, the in vitro methods involving iterative cycles of selection isolation and reamplification of the bound members of the library by PCR amplification are very time consuming. In contrast, the single cycle of split/pool synthesis, selection and identification of the present invention circumvents the need for the iterative cycles of amplification, isolation and reamplification. The split pool bead-based method and library of the present invention allows for the identification of the positions of any 3'-monothioate/dithioate linkages.

Although the beads were screened against a target protein labeled with a fluorescent dye, the beads can also be screened directly against the unmodified transcription factor. The binding of the NF-κB to a specific sequence can be detected using a primary anti-NF-κB antibody, followed by a secondary antibody conjugated to a marker molecules including fluorescein or rhodamine for fluorescence microscope (Yang, X. unpublished results).

To confirm the selection results, the S—ODN: 5'-CtGT-GAGtCGACTgAtGaCGGt-3' (SEQ ID NO.: 15)(small letters represent location of 3'-thioates), was independently synthesized on the non-cleavable linker bead support, hybridized with its complementary ODN and then mixed again with the NF-κB p50/p50 protein labeled with the Alexa Fluor 488 dye. The fluorescence intensity of all of the beads viewed under the fluorescence microscope was qualitatively similar to the intensity of the selected bead containing this sequence within the combinatorial library. These results demonstrate that the primer regions do not contribute to the binding of the NF-κB p50/50. Quantitative studies on the affinities of the selected S—ODNs and $S_2$—ODN duplexes to the protein along with selection from a large combinatorial library ($10^6 \sim 10^8$) to NF-κB are in progress.

In earlier studies a thioaptamer clone obtained from an in vitro combinatorial selection experiment (15 rounds of selection) bound to NF-κB p50/p50 with an apparent dissociation constant <5 nM (thiophosphate modification 5' to each dA residue: 5'-GGGGTTCCACCTTCACTGGGCG-3'•3'-CCCCAAGGTGGAAGTGACCCGC-5')(SEQ ID NOS:29 & 30). A chemically synthesized thioaptamer of the same sequence bound with a dissociation constant of <20 nM. It should be noted, however, that each chemically synthesized thioaptamer consists of a diasteromeric mixture containing $2^n$ different stereoisomers, where n is the number of thiophosphates ($2^7=128$ for the NF-κB p50/p50 selected thioaptamer). To determine the importance of the thiophosphate substitutions in the thioaptamer toward the NF-κB p50/p50 homodimer, a tight binding 15th round thioaptamer clone was synthesized by PCR with a nucleotide mix containing dATP instead of dATP($\alpha S$), and showed no binding of the normal phosphoryl backbone aptamer to NF-κB p50/p50 protein, supporting the critical role played by the thiophosphates.

Phosphoramidite chemistry has been widely used for the synthesis of S—ODNs because of its automation, high coupling efficiency and ease of site-specific thioate linkage incorporation. Synthesis of S—ODNs may be carried out by, e.g., forming an internucleoside phosphite linkage followed by sulfurization of the phosphite triester to a phosphorothioate. The resulting S—ODNs are a mixture of diastereoisomers, and consequently the diasteromeric S—ODN mixtures may have variable biochemical, biophysical and biological properties. Each bead then contains a library of monothioate aptamers (a library of libraries) since each bead contains the identical sequence and position of thiophosphate substitution, but represents a mixture of diastereomers introduced through the new monothiophosphate chiral centers. Stereocontrolled synthesis of a stereodefined S—ODN library may also be used to determine which is the best aptamer that binds to the protein, or may even be used to select a thioaptamer (or thioaptamer library) that has high affinity for the target protein or biomolecule. The binding data indicated that diastereoisomeric mixture libraries have good selectivity and affinity, although not as high as pure stereoisomers.

Another possible solution lies in the synthesis of modifications that are achiral at phosphorus, such as the above $S_2$—ODN thioaptamer library study. In addition dithioates appear to have greater "stickiness" to proteins than the thioates or unmodified ODN backbone.

The present invention may also be used to identify different nucleotide sequence(s) and/or to identify the backbone modification. S—ODN and $S_2$—ODN libraries were also created that differ only in the position of phosphate or dithioate but not in its base sequence. It is known that positions of thiophosphates in a mixed backbone S—ODN sequence can be determined by reaction of the S—ODN with iodoethanol followed by base catalyzed cleavage of the thiophosphate triester. The feasibility of this approach for identifying location of thioate linkages has been demonstrated by the present inventors, and is often independent of base sequence.

The search for other split synthesis, bead-based combinatorial libraries containing base modifications and hybrid backbones with phosphate ester, thioates, dithioates or potentially neutral methylphosphonates or even peptide nucleic acid chimeras with improved properties, such as enhanced binding-affinity to a specific protein, increased biological stability, and improved cellular uptake, may be achieved by the split synthesis combinatorial selection method described here.

By the split/pool method with two columns $2^N$ different members of the library for N split/pool steps have been created. More columns (M) may also be used with the present invention to permit synthesis of $M^N$ different beads with one unique thioaptamer sequence on each bead. The limit to the size of the combinatory library is the number of steps (N) and the number of columns (M) and of course the total number of beads, which generally is in the range of $10^6$ or more depending upon the size of the beads and synthesizer columns. Recently, aptamer beads on 15-20 μm beads was achieved (Yang, unpublished) and thus a 40-fold increase in the library size is possible. These results demonstrate that small bead sizes may be used effectively to produce more complex libraries at reduced cost and making more efficient use of reagents. The use of 15-20 μm beads also demonstrates the scalability of the present invention. Finally, these results demonstrate that library sizes comparable to those created by in vitro combinatorial selection methods by using mixtures of phosphoramidites/thiophosphoramidites (up to 8 different species) at selected positions in a given synthesis step may be created. The methodology of the invention may even be used to create a library of libraries of beads, each bead containing a library of any complexity. Using the present invention a screener may easily create $10^6$ beads with $10^8$ combinatorial library members on each bead—total diversity in principle is thus $10^{14}$, the same as in in vitro combinatorial selection libraries.

Sulfur substitution in aptamers alters the binding affinity and sequence that is obtained by in vitro combinatorial selection methods. Post-selection phosphorothioate modifications of in vitro combinatorially selected sequences can thus result in thioaptamers in which affinity cannot be reliably predicted. The simultaneous selection for both avoids this difficulty. The bead-based split synthesis, selection and PCR identification of combinatorial aptamer libraries now provides a means to combinatorially select both monothioate and dithioate variations on aptamers.

Flow cytometry sorting of thioaptamer bead-based library. The present inventors also demonstrated the successful application of high throughput/multi-color flow cytometry and bead sorting to screen aptamer bead libraries for those beads which bind to, e.g., a target protein. Modifications may be made to the flow cytometer to make it more amenable to bead identification and isolation. For example, bead fluorescence and forward scatter were the two parameters chosen for real-time characterization of each aptamer bead passing the first sort point of a custom-built flow cytometer/sorter. Other scanning and sorting parameters may be used to select, isolate, view, designate, characeterize, etc. the beads through a flow cytometer as will be apparent to those of skill in the art of cytometric analysis.

In operation, "positive" beads (contain thioaptamer-bound target protein, the target protein was fluorescent-labelled with Alexa 488 dye) were easily sorted from negative beads. Flow cytometry may be used to replace, e.g., visual fluorescence microscope identification of beads containing bound target protein and the need to isolate the individual "positive" beads with a micromanipulator. The flow-sorted "positive" beads can then be subjected to, e.g., one-bead PCR to identify the thioaptamer that binds the target protein. The sorted "positive" beads may also be subjected to SELDI-MS analysis to confirm the identity of the bound protein (via molecular ion characterization). In cases where the "positive" bead's thioaptamer might have bound not only the target protein but other proteins in a sample, e.g., a secondary or even tertiary, etc. protein, SELDI-MS may be used to identify this event through the detection of multiple molecular ions. These results demonstrate that fluorescently protein-labeled beads are detected and differentiated from one another in a flow system in order to, e.g., sort out certain portions of the beads.

as the present inventors have demonstrated previously use of the one-bead, one-ODN:protein system using dual color sorting (U.S. patent application Ser. No. 10/272,509, filed Oct. 16, 2002, relevant portions incorporated herein by reference). Breifly, the dsDNA κB consensus sequences in the Igκ gene were immobilized onto 15-20 micron polystyrene microspheres. The DNA bound beads were then incubated with purified NF-κB p50 and p65 proteins, respectively. DNA transcription factor complexes were detected with primary antibodies specific for the NF-κB p50 and p65 proteins followed by an additional incubation with Alexa 488-conjugated secondary antibody for NF-κB p50 and PE-conjugated secondary antibody for p65. The beads were viewed by fluorescent microscopy and then analyzed on the MCU's HiReCS system.

EXAMPLE II

ELISA Based Thioaptamer Selection-Indirect ELDIA

Although the beads were screened against a target protein labeled with a fluorescent dye, the beads can also been screened directly against the transcription factor. The binding of the NF-κB to a specific sequence can be detected using a primary anti-NF-κB antibody (Rabbit IgG antibody, Santa Cruz Biotechnology, Inc.) followed by a secondary antibody conjugated with Alexa Fluor 488 (goat anti-rabbit IgG from Molecular Probes). Next, several beads were selected for sequencing. The sequencing result were as follows:

```
E008 Selected sequences
5'-CGCCAGCCGaAGGTGCTGTCAG-3'    (SEQ ID NO:31)

5'-ATGTAGCCAaAGGTGgaACCCC-3'    (SEQ ID NO:32)

5'-CGCCcAGTgaAGGTGCTGTCAG-3'    (SEQ ID NO:33)

5'-CGCCcAGTAGCTAGTCTGTCAG-3'    (SEQ ID NO:34)
```

It was observed that the phosphorodithioate linkage (s) in the selected above sequences were different from those of the screening against the fluorescently labeled NF-κB p50. This result suggests that some of the binding sites of NF-κB p50 protein may be preoccupied by fluorescent molecules.

EXAMPLE III

Labeling of the ODN with Fluorescent Dyes

When synthesizing combinatorial libraries or specific thioaptamer sequences on beads, one may also identify beads by attaching 2 or more fluorescent dyes to the ODN either at the 5' or 3' ends or internally by using phosphoramidites with specific fluorophors attached. By using 1-3 (or more) fluorophors at 2-3 or more different levels (individual nucleosides), it is possible to identify dozens or more of the sequences or libraries by multicolor flow cytometry. (Each bead can thus be identified by dye A, B and/or C at levels high, medium, low in various combinations: thus bead with A(hi), B(medium) and C(low) would be one of dozens of different possible combinations.)

Thus it is possible to multiplex using flow cytometry or by randomly placing beads onto, e.g., the Texas tongue with hundreds or thousands or more of different microwell holders, random assortment of thioaptamer beads specific for binding different analytes. Alternatively, it is possible to label fluorescently cell extracts with another dye and then bind the protein(s) to the beads in conjunction with multicolor flow or surface fluorescence, multiplex diagnostics chip or beads, as described hereinbelow.

EXAMPLE IV

Fluorescent Tagging of Proteins Only with SELDI MS to Identify Proteins Expressed Differentially The thioaptamer combinatorial library may be used in conjunction with fluorescent tagging of proteins only and SELDI MS to identify proteins differentially expressed in control vs. experiment. In this simple two-color assay, a combinatorial library (or a combinatorial library of libraries) of beads is synthesized, each bead with a single thioaptamer sequence (or a combinatorial library of thioaptamer sequences on each bead). In this was we could create up to $10^8$ beads with a single thioaptamer sequence on each bead.

Cell extracts of a sample are labeled fluorescently with a dye (cy3 for example) and a control cell extract is labeled fluorescently with another dye (cy5 for example). Both cell extracts are mixed together and allowed to bind to the bead thioaptamer library. Next, two (2) color flow cytometry is used to compare cy3/cy5 color levels of each bead. If cy3/cy5 level differs from 1, then the bead may be captured. To determine which protein(s) have been bound to selected thioaptamer bead protein determination technique, e.g., SELDI MS may be used to characterize the bound target further. SELDI MS may be used to determine which proteins have been bound to selected combinatory thioaptamer libraries and also used with single bead PCR to identify which bead(s) in the combinatorial library have bound to protein(s). Pure thioaptamer beads may be placed or spotted onto a chip or used in conjunction with, e.g., flow cytometry methods to bind the protein expressed differentially in a sample relative to control.

EXAMPLE V

Fluorescent Tagging and SELDI to Identify Proteins Expressed Differentially

The thioaptamer combinatorial library may be used in conjunction with fluorescent tagging and SELDI to identify proteins differentially expressed in control vs. experiment. Combinatorial libraries of thioaptamer sequences on individual beads can be synthesized (for example at position N1 on a split synthesis column 1 use 33% of A, G and T while on column 2 use C thiophosphoramidite to introduce either normal mixture of A/G/T phosphates or C dithiophosphate which can be identified by sequencing the N1 position. In this fashion we could create up to $10^8$ beads with $10^{12}$ combinatorial library members on each bead—total diversity in principle is $10^{20}$ (of course the actually diversity is only about $10^{14}$ at best).

Alternatively, the user may create only 100 different split synthesis beads each with up to $10^{12}$ combinatorial library members on the beads. By using, e.g., 3 or more fluorophors, attached at various levels via phosphoramidite chemistry to the ODN it is possible to use flow cytometry to identify each bead library. For example, sample cell extracts may be labelled fluorescently with one dye (cy3 for example) and control cell extracts may be labelled fluorescently with another dye (cy5 for example). Use of five (5) color flow cytometry may also be used to compare cy3/cy5 color levels of each bead library that is identified by covalently attached flurophors to one or more of the thioaptamer(s). If cy3/cy5 level differs from 1, then sort the beads by the fluorophore tags for each non-unitary cy3/cy5 levels. As with the previous Example, SELDI MS may be used to determine which proteins have been bound to selected combinatory thioaptamer libraries and also used with single bead PCR to identify which bead(s) in the combinatorial library have bound to protein(s). In one embodiment of the present invention it is possible to incorporate a modified nt phosphoramidite (at the C-5 pyrimidine position for example) in the combinatorial library sequence positions to create a tag for the libraries and thus create 100 libraries in one split/pool synthesis. Alternatively, it is possible to use photoactivated crosslinkers to attach the protein to the thioaptamer (e.g., BrU on a single strand). Proteolysis of protein(s) may be used in conjunction with MS to identify the bound peptides and/or proteins. It is also possible, as described hereinabove, to use single-bead PCR to identify which bead(s) from the combinatorial library have bound to the protein(s). Since the BrU is on only 1 strand of the thioaptamer, the other can be sequenced by PCR. To identify the exact thioaptamer sequence that bound to the protein, then a four (4) column split/pool synthesizer may be needed. Alternatively, it is possible to spot pure thioaptamer or library onto chip and use this spot to bind the differentially expressed protein under the sample relative to control.

EXAMPLE VI

Synthesized a Monothio RNA Library

The present inventors have also successfully synthesized a monothio RNA library ($2^{15}$=32768). Standard phosphoramidite (DNA and RNA) chemistry was used for the monothio RNA library. A 0.5 M 1H-tetrazole in acetonitrile was used as DNA activator. A 0.5 M solution of DCI (dicyanoimidazole) in acetonitrile was used as RNA activator. The libraries were prepared on a 1 µmole scale of polystyrene beads (66-70 µm). The downstream and upstream primers, 5'-d(GGATCCGGTGGTCTG)-3' (SEQ ID NO:35) and 5'-d(CCTACTCGCGAATTC)-3' (SEQ ID NO:36) were synthesized in parallel on a two-column DNA synthesizer (Expedite 8909, Applied Biosystems). Following the 5'-primer, the sequences programmed on the synthesizer for the combinatorial mono RNA library were 5'-r(GA*UC*CU*GA*AA*CU*GU*UW*UA*AG*GU*UG*GC*CG*AU*C)-3' (SEQ ID NO:37) on column 1 and 5'-r(cU*aG*gA*cU*uG*gC*aC*aA*cC*gU*cA*cA*cU*gC*uA*u)-3' (SEQ ID NO:38) on column 2. The 3'-primer sequence completed the 61-mer programmed on the synthesizer.

A "split and pool" occurred at each position indicated by an asterisk in order to synthesize the combinatorial region for the monothio RNA. The lower case letter indicates a 3'-thioate linkage, the upper case letter indicates a 3'-phosphate linkage. The coupling yield was typically upwards of 98.5% as determined by the dimethoxytrityl cation assay. Sulfurization chemistry utilized the Beaucage reagent. The fully protected monothio RNA combinatorial library with the non-cleavable linker beads were treated with 4 ml of a mixture of 3:1 (v/v) (28%) $NH_3$: EtOH at 39° C. for 21 hrs. The beads were centrifuged, the supernatant was removed and the solid support was washed with double-distilled water. After lyophilization the solid support was treated with 2 ml of triethylamine trihydrofluoride (TEA-3HF) for 20 hrs at room temperature. Again, the beads were centrifuged, the supernatant was removed and the solid support was washed with double-distilled water.

```
Column 1:
5'-CCTACTCGCGAATTC-GA*UC*CU*GA*AA*    (SEQ ID NO:39)
CU*GU*UU*UA*AG*GU*UG*GC*CG*AU*C-      Phosphate
GGATCCGGTGGTCTG-Linker-3':

Column 2:
5'-CCTACTCGCGAATTC-CU*AG*GA*CU*UG*    (SEQ ID NO:40):
GC*AC*AA*CC*GU*CA*CU*GC*UA*G-         MonothioRNA
GGATCCGGTGGTCTG-Linker-3'
```

EXAMPLE VII

NMR Spectra of XBY-5 and XBY-15

The NOESY, DQCOSY and TOCSY spectra of XBY-2, XBY-6, XBY-5 (200 OD) and XBY-15 (90 OD) have been acquired. NMR structures for XBY-2 and XBY-6 have been deterninined and shown to differ from the structure of the parent duplex sequence without any dithioate substitutions (Volk, et al., in press). The structures of the other two thioaptamers are being determined.

```
XBY-5:
5'-CC AGGAGAT_{S2}T_{S2}CCA C-3'          (SEQ ID NO:41)

3'-GG_{S2}TCC TCTA A GG_{S2}TG-5'         (SEQ ID NO:42)

XBY-15:
5'-CC A_{S2}G_{S2}GA GAT_{S2}T_{S2}CCAC-3'  (SEQ ID NO:43)

3'-GGT_{S2}C_{S2}CT_{S2}CTA A GGTG-5'      (SEQ ID NO:44)
```

EXAMPLE VIII

High Quality of One-bead, One-ODN Library Ligation Reaction

The present inventors demonstrated that they could construct high quality one-bead one-oligo libraries by join two pieces of DNA based on ligation reaction or highly active phosphorothioate towards 5'-iodo groups on the ODN. Standard phosphoramidite chemistry was used for synthesis of 5' monophosphate ODN (5'-P(o)CCAGGAGATTCCACGG-ATCCGGTGGTCTGT-bead) (SEQ ID NO:45). The fully protected ODN with the non-cleavable linker beads were treated with concentrated ammonia at 37° C. for 21 hours to remove the protecting groups while allowing the ODN to remain attached to the beads. A selected single bead was mixed with the following components: 3 µl of 40 µM 15mer oligonucleotide (5'-CCTACTCGCGAATTC-3' (SEQ ID NO:36), 3 µl of 10× ligation buffer, 3 µl of DMSO, 2 µl of T4 RNA ligase and 19 µl of dd$H_2O$. The reaction was performed at 5° C. for 17 hrs. The supernatant was removed carefully and washed with water. The single bead was performed PCR reaction at established conditions. The PCR products were analyzed on a 15% native polyacrylamide gel. The PCR product was cloned using the TA Cloning procedure (Invitrogen) and sequenced on an ABI Prism 310 Genetic Analyzer (Applied Biosystems). The desired sequence (5'-CCTACTCGCGAATTC-P(o)CCAGGAGAT-TCCACGGATCCGGTGGTCTGT-bead) (SEQ ID NO:46), was obtained.

To demonstrate the ligation reaction, a simple ODN was ligated to a single bead of a one-bead, one-ODN library, namely:

```
5'-CCTACTCGCGAATTC-3'  +  5'-P(o)CCAGGAGATTCCAC-GGATCCGGTGGTCTGT-3'-    (SEQ ID NOS:36, 45)
                                                              BEAD
                                    ↓
       5'-CCTACTCGCGAATTC-P(o)CCAGGAGATTCCAC-GGATCCGGTGGTCTGT-3'-        (SEQ ID NO:46)
                                                              BEAD
```

The ligation reaction was confirmed by one-bead PCR reaction and cloning and sequencing. These results show that the additional nucleic acid sequences may be added to one or more of the beads of a one-bead, one-ODN library with high quality and efficiency while maintaining the integrity of the library. The ligation reaction allows longer random regions of aptamers to be synthesized on the beads with higher yield since a primer region does not have to be stepwise synthesized onto the bead sequence.

EXAMPLE IX

Separation of Synthetic Oligonucleotide Dithioates from Monothiophosphate Impurities by Anion-exchange Chromatography on a Mono Q Column A method using a strong anion-exchange liquid chromatography column, Mono Q, has been developed for high resolution analysis and purification of oligonucleotide dithioates, which were synthesized by an automated, solid-phase, phosphorothioamidite chemistry. High-resolution separation of oligonucleotide phosphorodithioates from monothiophosphate impurities was obtained. High-resolution separation was also demonstrated at pH 8. The separation of oligonucleotide dithioates was found to be linearly dependent on the number of sulfurs for the same sequence length. Thiocyanate, SCN$^-$, as eluting anion, can be used to purify oligonucleotides containing a high percentage of phosphorodithioate linkages in lower salt concentration, and provide better separation than that of chloride as eluting anion.

Synthesis of oligomers. The following oligomers were synthesized for this study:

```
New Scramble:
5'-CCA GT_{S2}GA CT_{S2}CA GT_{S2}G-3'           (SEQ ID NO:47)

3'-GGT_{S2}CA CT_{S2}GA GT_{S2}CA C-5'           (SEQ ID NO:48)

5'-amino-xby6:
5'-H_2NC_{12}H_{24}-O_3P-O-CCAGG A GA            (SEQ ID NO:49)
T_{S2}T_{S2}CCA C-3'

3'-GGT_{S2}CCT_{S2}CT_{S2}A A GGT_{S2}G-5'       (SEQ ID NO:50)

5'-fluorescein-xby6:
5'-C_6H_{12}-O_3P-O-CCA GGA GA T_{S2}T_{S2}CCA   (SEQ ID NO:51)
C-3',

3'-GGT_{S2}CCT_{S2}CT_{S2}A A GGT_{S2}G-5'       (SEQ ID NO:52)
```

XBY-6 and IgkB-22 on Beads for:

```
5'-AGTTGAGGGGACTTTCCCAGGCTT-bead                 (SEQ ID NO:53)
(IgkB)

3'-TCAACTCCCCTGAAAGGGTCCG-5'                    (SEQ ID NO:54)

5'-CC AGG AG AT_{S2}T_{S2}CC AC-linker-          (SEQ ID NO:55)
bead (XBY-6)

3'-GG_{S2}TCC_{S2}TC_{S2}T A A GG_{S2}TG-5'      (SEQ ID NO:56)
```

XBY20-26 for EMSA Competition Assay

```
XBY-20: dithioP50-1:    5'-CGC CC_{S2}A GTG_{S2}A_{S2}AG GTG G_{S2}A_{S2}A    (SEQ ID NO:57)
                        CCCC-3' dithioP50-1c:   5'-GGG GTT CC_{S2}A C CTT C_{S2}AC TGG                 (SEQ ID NO:58)
                        GCG-3'

XBY-21: dithioP50-2:    5'-CGC CC_{S2}A GTG_{S2}AAG GTG GA_{S2}A               (SEQ ID NO:59)
                        CCCC-3' dithioP50-1c:   5'-GGG GTT CC_{S2}A C CTT C_{S2}AC TGG                 (SEQ ID NO:60)
                        GCG-3'

XBY-22: dithioP50-3:    5'-CGC CC_{S2}A GTGAAG GTG GA_{S2}A                    (SEQ ID NO:61)
                        CCCC-3' dithioP50-1c:   5'-GGG GTT CC_{S2}A C CTT C_{S2}AC TGG                 (SEQ ID NO:62)
                        GCG-3'

XBY-23: dithioP50-1:    5'-CGC CC_{S2}A GTG_{S2}A_{S2}AG GTG G_{S2}A_{S2}A     (SEQ ID NO:63)
                        CCCC-3' phosphateP50-1c: 5'-GGG GTT CCA C CTT C AC TGG GCG-3'                  (SEQ ID NO:64)

XBY-24: dithioP50-2:    5'-CGC CC_{S2}A GTG_{S2}AAG GTG GA_{S2}A               (SEQ ID NO:65)
                        CCCC-3' phosphateP50-1c: 5'-GGG GTT CCA C CTT C AC TGG GCG-3'                  (SEQ ID NO:66)

XBY-25: dithioP50-3:    5'-CGC CC_{S2}A GTGAAG GTG GA_{S2}A                    (SEQ ID NO:67)
                        CCCC-3' phosphateP50-1c: 5'-GGG GTT CCA C CTT C AC TGG GCG-3'                  (SEQ ID NO:68)

XBY-26: PhosphateP50-1: 5'-CGC CCA GTGAAG GTG GAA CCCC-3'                      (SEQ ID NO:69)

dithioP50-1c:   5'-GGG GTT CC_{S2}A C CTT C_{S2}AG TGG                 (SEQ ID NO:70)
                        GCG-3'
```

It was found that the XBY20-26 ODN does not compete as well as the selected oligo (monothio selected) with the recombinant NF-κB p50. The chemically synthesized selected oligo (2) was the best so far.

EXAMPLE X

Figure 8:
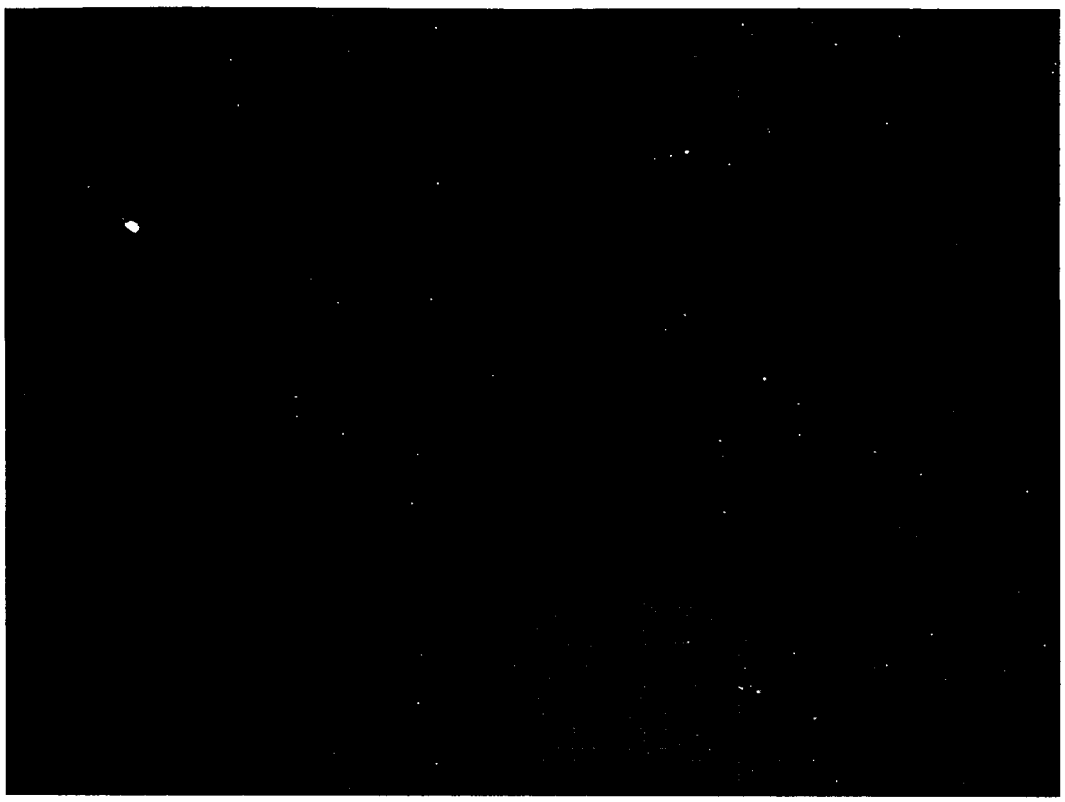
FIG. 8 is a photomicrograph of gel without beads.
Figure 9:
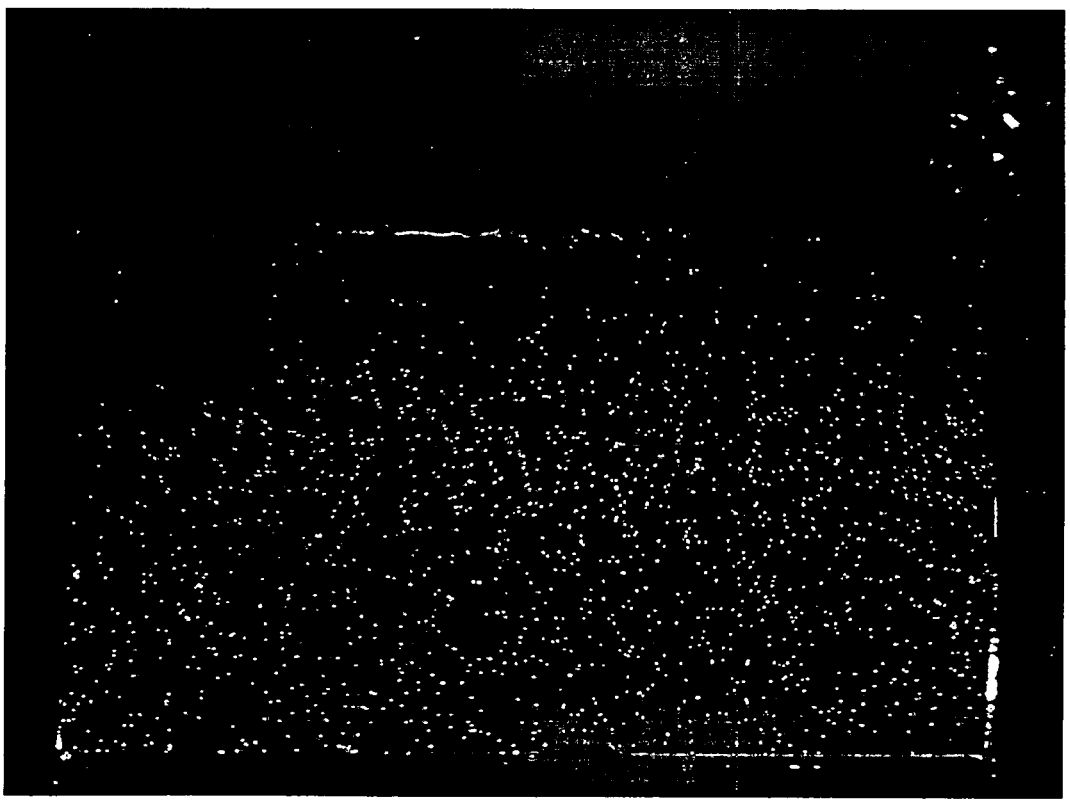
FIG. 9 is a photomicrograph of gel in which was dispersed 50 ul of fluorescent-labeled beads (approximately $1.4 \times 10^4$ beads.
Figure 10:
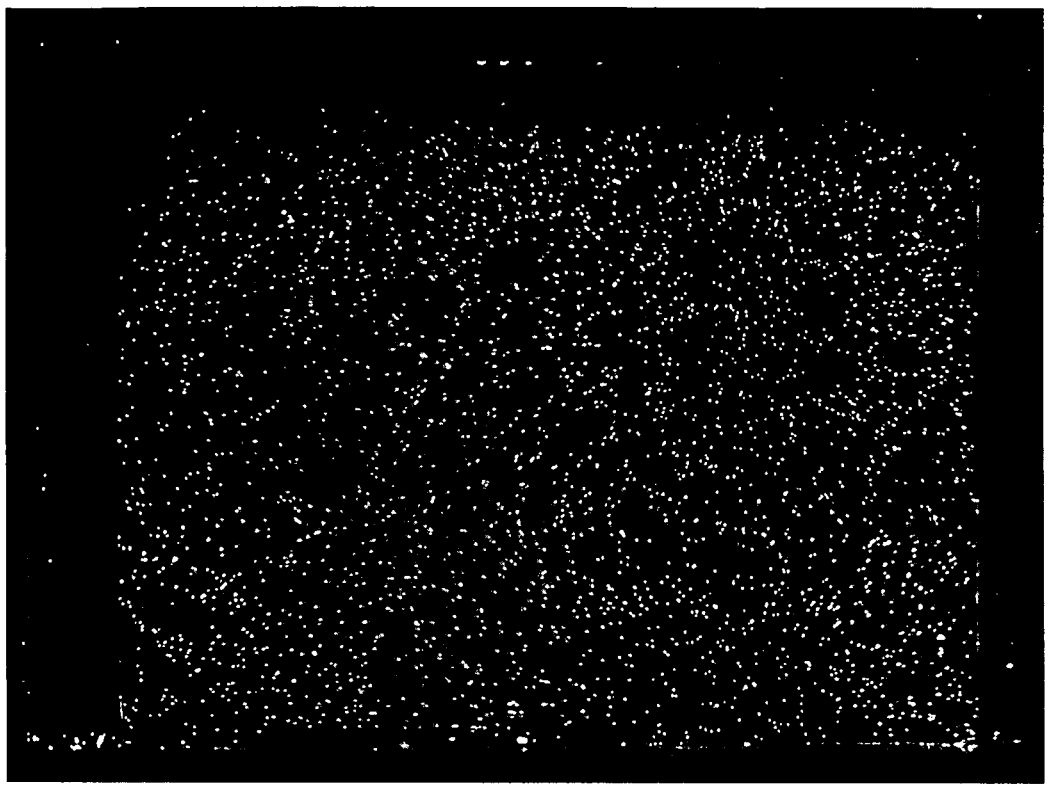
FIG. 10 is a photomicrograph of gel in which was dispersed 100 ul of fluorescent-labeled beads (approximately $3 \times 10^4$ beads)
Figure 11:
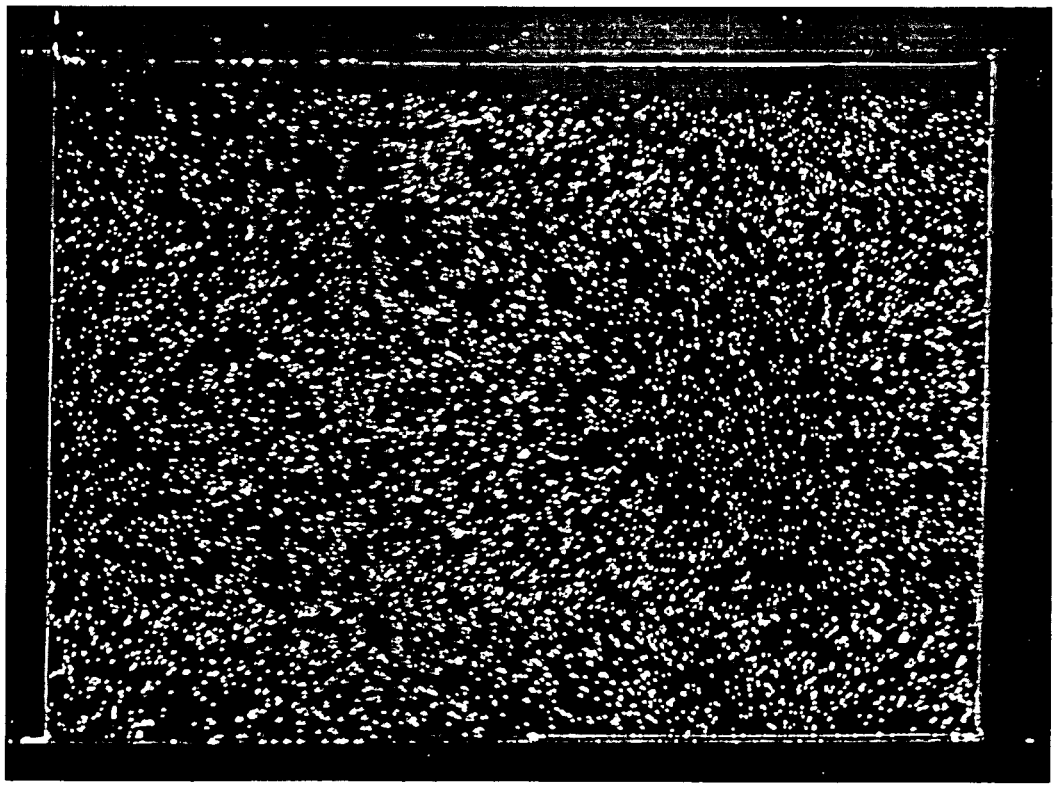
FIG. 11 is a photomicrograph of gel in which was dispersed 150 ul of fluorescent-labeled beads (approximately $4.2 \times 10^4$ beads).

Dispersal and imaging of fluorescent-labelled microbeads within a thixotropic gel 50 uL, 100 uL and 150 uL of fluorescently labelled 66 micron beads, that includes approximately 14,000, 30,000 and 42,000 beads, respectively, were each added to approximately 5 uL of 15% PAGE-GEL solution. Each bead-gel solution was vortexed and then 5 uL, 10 uL and 15 uL of TEMED (tetramethylene diamine) gel polymerization catalyst was added to each vortexed solution, respectively, and the bead-gel was immediately loaded onto a Bio-Rad mini-gel system. The 7×10 cm gels, of 0.7 mm thickness, were then viewed on a Perkin-Elmer ProEXpress 2D gel imager. FIG. 8 shows the image of a gel treated as above, but without the addition of the fluorescent beads, thus acting as the control image. FIGS. 9-11 show the images of the bead-gels having 14,000, 30,000 and 42,000 beads. The beads are relatively uniformly dispersed in all three images. FIGS. 8-11 demonstrate feasibility of uniformly dispersing the aptamer beads within a thixotropic 2D gel matrix and of imaging the bead-gels via detection of the fluorescence of the labelled beads, providing the signal and image location that can be used by a commercialy available robotic spot picker to address beads of interest and both chemically and mechanically manipulate such beads.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description.

What is claimed is:

1. A method for isolation of a target comprising the steps of:
dispersing one or more probe beads comprising a thioaptamer library selected from thioaptamers (S—ODN) or dithioaptamers (S$_2$—ODN) in a thixotropic agent, wherein the thioaptamers comprises one or more but less than all of the linkages selected from the group rATP($\alpha$S$_2$), rUTP($\alpha$S$_2$), rGTP($\alpha$S$_2$), rCTP($\alpha$S$_2$), rATP($\alpha$S), dTTP($\alpha$S), dGTP($\alpha$S), dCTP($\alpha$S), dATP($\alpha$S$_2$), dTTP($\alpha$S$_2$), dGTP($\alpha$S$_2$) and dCTP($\alpha$S$_2$);
scanning for probe beads that generate a detectable signal from interaction between the one or more probe beads and the target; and
picking one or more probe beads based on the detectable signal;
extracting the target from the probe bead; and
identifying the target by mass spectrometry after liquid chromatography.

2. The method of claim 1, further comprising the step of identifying the target using mass spectrometry comprises matrix assisted laser desorption ionization mass spectrometry.

3. The method of claim 1, wherein each of the probe beads are further modified to comprise a colorimetric agent.

4. The method of claim 1, wherein each of the probe beads further comprise one or more bases that are attached to a fluorophor.

5. The method of claim 1, wherein each of the probe beads further comprises one or more fluorophors attached to the 5' end, the 3' end or internally within the thioaptamers (S—ODN) or the dithioaptamers (S$_2$—ODN).

6. The method of claim 1, wherein the target is labeled with a fluorescent agent.

7. The method of claim 1, wherein the probe bead is acquired by a scanning robotic head and the target is extracted from the probe bead in situ.

8. The method of claim 1, wherein the probe bead is acquired by a scanning robotic head and the target is extracted from the probe bead in situ by proteolysis and transferred to an inlet of an LC-MS or an LC-MS/MS.

9. The method of claim 1, wherein the probe bead is acquired by a scanning robotic head and the target is extracted from the probe bead in situ for MALDI-MS analysis, wherein the MALDI-MS analysis is MALDI-TOF/MS.

10. The method of claim 1, wherein the probe bead is acquired by a scanning robotic head and the target is extracted from the probe bead in situ for LC-MS analysis.

11. The method of claim 1, wherein the probe bead is acquired by a scanning robotic head and the target is extracted from the probe bead in situ for MALDI-MS analysis.

12. The method of claim 1, wherein the probe bead is acquired by a scanning robotic head and the target is extracted from the probe bead in situ for MALDI-MS analysis by SELDI ionization.

13. The method of claim 1, wherein the probe bead is further processed to remove the target bound to the aptamer bead and analyzing the target by binding a second detectable label to the target.

14. The method of claim 1, wherein the thixotrophic agent comprises a polyacrylamide gel.

15. The method of claim 1, wherein picking the one or more probes beads is semi-manually.

16. The method of claim 1, wherein the target is a protein.

17. The method of claim 1, wherein the one or more probe beads are dispersed within the thixotropic agent by molecular printing.

18. The method of claim 1, wherein the one or more probe beads are dispersed within the thixotropic agent using an ink-jet printer.

* * * * *

UNITED STATES PATENT AND TRADEMARK OFFICE
CERTIFICATE OF CORRECTION

PATENT NO. : 7,338,762 B2 Page 1 of 1
APPLICATION NO. : 10/828935
DATED : March 4, 2008
INVENTOR(S) : Gorenstein et al.

It is certified that error appears in the above-identified patent and that said Letters Patent is hereby corrected as shown below:

Title Page, Item (60), Related U.S. Application Data "Provisional application No. 60/334,887, filed on Nov. 15, 2001" should be deleted.

Column 1, Line 8-9, "and a continuation in part of U.S. Provisional Patent Application No. 60/334,887, filed Nov. 15, 2001" should be deleted.

Signed and Sealed this

Twenty-third Day of September, 2008

JON W. DUDAS
*Director of the United States Patent and Trademark Office*

SEQUENCE LISTING

```
<160> NUMBER OF SEQ ID NOS: 70

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      polynucleotide primer

<400> SEQUENCE: 1
ggatccggtg gtctg                                                          15

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      polynucleotide primer

<400> SEQUENCE: 2
cctactcgcg aattc                                                          15

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 3
cagttgaggg gactttccca ggc                                                 23

<210> SEQ ID NO 4
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (1)..(2)
<223> OTHER INFORMATION: 3' thioate linkage
<220> FEATURE:
<221> NAME/KEY: misc_feature
<222> LOCATION: (3)..(4)
<223> OTHER INFORMATION: 3' thioate linkage
<220> FEATURE:
<221> NAME/KEY: misc_feature
<222> LOCATION: (5)..(6)
<223> OTHER INFORMATION: 3' thioate linkage
<220> FEATURE:
<221> NAME/KEY: misc_feature
<222> LOCATION: (7)..(8)
<223> OTHER INFORMATION: 3' thioate linkage
<220> FEATURE:
<221> NAME/KEY: misc_feature
<222> LOCATION: (9)..(10)
<223> OTHER INFORMATION: 3' thioate linkage
<220> FEATURE:
<221> NAME/KEY: misc_feature
<222> LOCATION: (11)..(12)
<223> OTHER INFORMATION: 3' thioate linkage
<220> FEATURE:
<221> NAME/KEY: misc_feature
<222> LOCATION: (13)..(14)
<223> OTHER INFORMATION: 3' thioate linkage
<220> FEATURE:
<221> NAME/KEY: misc_feature
<222> LOCATION: (15)..(16)
<223> OTHER INFORMATION: 3' thioate linkage
<220> FEATURE:
<221> NAME/KEY: misc_feature
<222> LOCATION: (17)..(18)
<223> OTHER INFORMATION: 3' thioate linkage
<220> FEATURE:
<221> NAME/KEY: misc_feature
<222> LOCATION: (19)..(20)
<223> OTHER INFORMATION: 3' thioate linkage
<220> FEATURE:
<221> NAME/KEY: misc_feature
<222> LOCATION: (21)..(22)
<223> OTHER INFORMATION: 3' thioate linkage
<220> FEATURE:
<221> NAME/KEY: misc_feature
<222> LOCATION: (23)
<223> OTHER INFORMATION: 3' thioate to base

<400> SEQUENCE: 4
cctgcacatc tcaggatgac ttt                                               23

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 5
atgtagccag ctagtctgtc ag                                                22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence
```

```
<220> FEATURE:
<221> NAME/KEY: misc_feature
<222> LOCATION: (5)..(6)
<223> OTHER INFORMATION: 3' dithioate linkage
<220> FEATURE:
<221> NAME/KEY: misc_feature
<222> LOCATION: (9)..(10)
<223> OTHER INFORMATION: 3' dithioate linkage
<220> FEATURE:
<221> NAME/KEY: misc_feature
<222> LOCATION: (10)..(11)
<223> OTHER INFORMATION: 3' dithioate linkage
<220> FEATURE:
<221> NAME/KEY: misc_feature
<222> LOCATION: (16)..(17)
<223> OTHER INFORMATION: 3' dithioate linkage
<220> FEATURE:
<221> NAME/KEY: misc_feature
<222> LOCATION: (19)..(20)
<223> OTHER INFORMATION: 3' phosphate linkage

<400> SEQUENCE: 6
cgcccagtga aggtggaacc cc                                            22

<210> SEQ ID NO 7
<211> LENGTH: 50
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 7
atgcctactc gcgaattccc aggagattcc acggatccgg tggtctgttc              50

<210> SEQ ID NO 8
<211> LENGTH: 52
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 8
cctactcgcg aattcagttg aggggacttt cccaggcgga tccggtggtc tg            52

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      polynucleotide primer

<400> SEQUENCE: 9
atgcctactc gcgaattc                                                 18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      polynucleotide primer

<400> SEQUENCE: 10
gaacagacca ccggatcc                                                 18
```

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 11
ctgtgagtcg actgatgacg gt                                              22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 12
agttgagtcg aaggacccat tt                                              22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 13
cgtcaagtct cagttcccat tt                                              22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 14
agtcaagtcg aagttccacg gt                                              22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (2)..(3)
<223> OTHER INFORMATION: 3' thioate linkage
<220> FEATURE:
<221> NAME/KEY: misc_feature
<222> LOCATION: (8)..(9)
<223> OTHER INFORMATION: 3' thioate linkage
<220> FEATURE:
<221> NAME/KEY: misc_feature
<222> LOCATION: (14)..(15)
<223> OTHER INFORMATION: 3' thioate linkage
<220> FEATURE:
<221> NAME/KEY: misc_feature
<222> LOCATION: (16)..(17)
<223> OTHER INFORMATION: 3' thioate linkage
<220> FEATURE:
<221> NAME/KEY: misc_feature
<222> LOCATION: (18)..(19)
<223> OTHER INFORMATION: 3' thioate linkage

```
<220> FEATURE:
<221> NAME/KEY: misc_feature
<222> LOCATION: (22)
<223> OTHER INFORMATION: 3' thioate to base

<400> SEQUENCE: 15
ctgtgagtcg actgatgacg gt                                              22

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (8)..(9)
<223> OTHER INFORMATION: 3' thioate linkage
<220> FEATURE:
<221> NAME/KEY: misc_feature
<222> LOCATION: (12)..(13)
<223> OTHER INFORMATION: 3' thioate linkage
<220> FEATURE:
<221> NAME/KEY: misc_feature
<222> LOCATION: (14)..(15)
<223> OTHER INFORMATION: 3' thioate linkage
<220> FEATURE:
<221> NAME/KEY: misc_feature
<222> LOCATION: (20)..(21)
<223> OTHER INFORMATION: 3' thioate linkage
<220> FEATURE:
<221> NAME/KEY: misc_feature
<222> LOCATION: (22)
<223> OTHER INFORMATION: 3' thioate to base

<400> SEQUENCE: 16
agttgagtcg aaggacccat tt                                              22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (4)..(5)
<223> OTHER INFORMATION: 3' thioate linkage
<220> FEATURE:
<221> NAME/KEY: misc_feature
<222> LOCATION: (8)..(9)
<223> OTHER INFORMATION: 3' thioate linkage
<220> FEATURE:
<221> NAME/KEY: misc_feature
<222> LOCATION: (10)..(11)
<223> OTHER INFORMATION: 3' thioate linkage
<220> FEATURE:
<221> NAME/KEY: misc_feature
<222> LOCATION: (12)..(13)
<223> OTHER INFORMATION: 3' thioate linkage
<220> FEATURE:
<221> NAME/KEY: misc_feature
<222> LOCATION: (20)..(21)
<223> OTHER INFORMATION: 3' thioate linkage
<220> FEATURE:
<221> NAME/KEY: misc_feature
<222> LOCATION: (22)
<223> OTHER INFORMATION: 3' thioate to base

<400> SEQUENCE: 17
cgtcaagtct cagttcccat tt                                              22
```

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (4)..(5)
<223> OTHER INFORMATION: 3' thioate linkage
<220> FEATURE:
<221> NAME/KEY: misc_feature
<222> LOCATION: (8)..(9)
<223> OTHER INFORMATION: 3' thioate linkage
<220> FEATURE:
<221> NAME/KEY: misc_feature
<222> LOCATION: (12)..(13)
<223> OTHER INFORMATION: 3' thioate linkage
<220> FEATURE:
<221> NAME/KEY: misc_feature
<222> LOCATION: (18)..(19)
<223> OTHER INFORMATION: 3' thioate linkage
<220> FEATURE:
<221> NAME/KEY: misc_feature
<222> LOCATION: (22)
<223> OTHER INFORMATION: 3' thioate to base

<400> SEQUENCE: 18
agtcaagtcg aagttccacg gt                                      22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 19
atgtagccag ctagtctgtc ag                                      22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 20
cgccagccaa aggtgctgtc ag                                      22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 21
cgcccagtgg ctagtgaacc cc                                      22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic -continued

```
      polynucleotide sequence

<400> SEQUENCE: 22
atgtagccga aggtggaacc cc                                              22

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 23
cgccagccga aggtggaacc cc                                              22

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 24
atgtagccag ctagtctgtc ag                                              22

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (10)..(11)
<223> OTHER INFORMATION: 3' dithioate linkage

<400> SEQUENCE: 25
cgccagccaa aggtgctgtc ag                                              22

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (5)..(6)
<223> OTHER INFORMATION: 3' dithioate linkage
<220> FEATURE:
<221> NAME/KEY: misc_feature
<222> LOCATION: (9)..(10)
<223> OTHER INFORMATION: 3' dithioate linkage
<220> FEATURE:
<221> NAME/KEY: misc_feature
<222> LOCATION: (16)..(18)
<223> OTHER INFORMATION: 3' dithioate linkage

<400> SEQUENCE: 26
cgcccagtgg ctagtgaacc cc                                              22

<210> SEQ ID NO 27
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (9)..(11)
<223> OTHER INFORMATION: 3' dithioate linkage
<220> FEATURE:
<221> NAME/KEY: misc_feature
<222> LOCATION: (16)..(18)
<223> OTHER INFORMATION: 3' dithioate linkage

<400> SEQUENCE: 27
atgtagccga aggtggaacc cc                                              22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (9)..(11)
<223> OTHER INFORMATION: 3' dithioate linkage
<220> FEATURE:
<221> NAME/KEY: misc_feature
<222> LOCATION: (16)..(18)
<223> OTHER INFORMATION: 3' dithioate linkage

<400> SEQUENCE: 28
cgccagccga aggtggaacc cc                                              22

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 29
ggggttccac cttcactggg cg                                              22

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 30
cgcccagtga aggtggaacc cc                                              22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (10)..(11)
<223> OTHER INFORMATION: 3' dithioate linkage

<400> SEQUENCE: 31
cgccagccga aggtgctgtc ag                                              22
```

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (10)..(11)
<223> OTHER INFORMATION: 3' dithioate linkage
<220> FEATURE:
<221> NAME/KEY: misc_feature
<222> LOCATION: (16)..(18)
<223> OTHER INFORMATION: 3' dithioate linkage

<400> SEQUENCE: 32
atgtagccaa aggtggaacc cc                                          22

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (5)..(6)
<223> OTHER INFORMATION: 3' dithioate linkage
<220> FEATURE:
<221> NAME/KEY: misc_feature
<222> LOCATION: (9)..(11)
<223> OTHER INFORMATION: 3' dithioate linkage

<400> SEQUENCE: 33
cgcccagtga aggtgctgtc ag                                          22

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (5)..(6)
<223> OTHER INFORMATION: 3' dithioate linkage

<400> SEQUENCE: 34
cgcccagtag ctagtctgtc ag                                          22

<210> SEQ ID NO 35
<211> LENGTH: 15
<212> TYPE: DNA
<213> ORGANISM: Artificial Sequence
<220> FEATURE:
<223> OTHER INFORMATION: Description of Artificial Sequence: Synthetic
      polynucleotide primer

<400> SEQUENCE: 35
ggatccggtg gtctg                                                  15

<210> SEQ ID NO 36
<211> LENGTH: 15
<212> TYPE: DNA
<213> ORGANISM: Artificial Sequence
<220> FEATURE:

<223> OTHER INFORMATION: Description of Artificial Sequence: Synthetic
      polynucleotide primer

<400> SEQUENCE: 36
cctactcgcg aattc                                                           15

<210> SEQ ID NO 37
<211> LENGTH: 31
<212> TYPE: RNA
<213> ORGANISM: Artificial Sequence
<220> FEATURE:
<223> OTHER INFORMATION: Description of Artificial Sequence: Synthetic
      polynucleotide sequence

<400> SEQUENCE: 37
gauccugaaa cuguuuaag guuggccgau c                                          31

<210> SEQ ID NO 38
<211> LENGTH: 31
<212> TYPE: RNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (1)..(2)
<223> OTHER INFORMATION: 3' thioate linkage
<220> FEATURE:
<221> NAME/KEY: misc_feature
<222> LOCATION: (3)..(4)
<223> OTHER INFORMATION: 3' thioate linkage
<220> FEATURE:
<221> NAME/KEY: misc_feature
<222> LOCATION: (5)..(6)
<223> OTHER INFORMATION: 3' thioate linkage
<220> FEATURE:
<221> NAME/KEY: misc_feature
<222> LOCATION: (7)..(8)
<223> OTHER INFORMATION: 3' thioate linkage
<220> FEATURE:
<221> NAME/KEY: misc_feature
<222> LOCATION: (9)..(10)
<223> OTHER INFORMATION: 3' thioate linkage
<220> FEATURE:
<221> NAME/KEY: misc_feature
<222> LOCATION: (11)..(12)
<223> OTHER INFORMATION: 3' thioate linkage
<220> FEATURE:
<221> NAME/KEY: misc_feature
<222> LOCATION: (13)..(14)
<223> OTHER INFORMATION: 3' thioate linkage
<220> FEATURE:
<221> NAME/KEY: misc_feature
<222> LOCATION: (15)..(16)
<223> OTHER INFORMATION: 3' thioate linkage
<220> FEATURE:
<221> NAME/KEY: misc_feature
<222> LOCATION: (17)..(18)
<223> OTHER INFORMATION: 3' thioate linkage
<220> FEATURE:
<221> NAME/KEY: misc_feature
<222> LOCATION: (19)..(20)
<223> OTHER INFORMATION: 3' thioate linkage
<220> FEATURE:
<221> NAME/KEY: misc_feature
<222> LOCATION: (21)..(22)
<223> OTHER INFORMATION: 3' thioate linkage
<220> FEATURE:
<221> NAME/KEY: misc_feature
<222> LOCATION: (23)..(24)
<223> OTHER INFORMATION: 3' thioate linkage
<220> FEATURE:
<221> NAME/KEY: misc_feature
<222> LOCATION: (25)..(26)

```
<223> OTHER INFORMATION: 3' thioate linkage
<220> FEATURE:
<221> NAME/KEY: misc_feature
<222> LOCATION: (27)..(28)
<223> OTHER INFORMATION: 3' thioate linkage
<220> FEATURE:
<221> NAME/KEY: misc_feature
<222> LOCATION: (29)..(30)
<223> OTHER INFORMATION: 3' thioate linkage
<220> FEATURE:
<221> NAME/KEY: misc_feature
<222> LOCATION: (31)
<223> OTHER INFORMATION: 3' thioate to base

<400> SEQUENCE: 38
cuaggacuug gcacaaccgu cacacugcua u                              31

<210> SEQ ID NO 39
<211> LENGTH: 61
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<223> OTHER INFORMATION: see specification for detailed description of
      preferred embodiments

<400> SEQUENCE: 39
cctactcgcg aattcgaucc ugaaacuguu uuaagguugg ccgaucggat ccggtggtct    60
g                                                                   61

<210> SEQ ID NO 40
<211> LENGTH: 61
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<223> OTHER INFORMATION: see specification for detailed description of
      preferred embodiments

<400> SEQUENCE: 40
cctactcgcg aattccuagg acuuggcaca accgucacac ugcuagggat ccggtggtct    60
g                                                                   61

<210> SEQ ID NO 41
<211> LENGTH: 14
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (9)..(11)
<223> OTHER INFORMATION: 3' dithioate linkage

<400> SEQUENCE: 41
ccaggagatt ccac                                                     14

<210> SEQ ID NO 42
<211> LENGTH: 14
<212> TYPE: DNA
<213> ORGANISM: Artificial Sequence
<220> FEATURE:
<223> OTHER INFORMATION: Description of Artificial Sequence: Synthetic
      polynucleotide sequence
```

```
<220> FEATURE:
<221> NAME/KEY: misc_feature
<222> LOCATION: (2)..(3)
<223> OTHER INFORMATION: 3' dithioate linkage
<220> FEATURE:
<221> NAME/KEY: misc_feature
<222> LOCATION: (12)..(13)
<223> OTHER INFORMATION: 3' dithioate linkage

<400> SEQUENCE: 42
gtggaatctc ctgg                                                   14

<210> SEQ ID NO 43
<211> LENGTH: 14
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (3)..(5)
<223> OTHER INFORMATION: 3' dithioate linkage
<220> FEATURE:
<221> NAME/KEY: misc_feature
<222> LOCATION: (9)..(11)
<223> OTHER INFORMATION: 3' dithioate linkage

<400> SEQUENCE: 43
ccaggagatt ccac                                                   14

<210> SEQ ID NO 44
<211> LENGTH: 14
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (8)..(9)
<223> OTHER INFORMATION: 3' dithioate linkage
<220> FEATURE:
<221> NAME/KEY: misc_feature
<222> LOCATION: (10)..(12)
<223> OTHER INFORMATION: 3' dithioate linkage

<400> SEQUENCE: 44
gtggaatctc ctgg                                                   14

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 45
ccaggagatt ccacggatcc ggtggtctgt                                  30

<210> SEQ ID NO 46
<211> LENGTH: 45
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 46
```

```
cctactcgcg aattcccagg agattccacg gatccggtgg tctgt          45
```

<210> SEQ ID NO 47
<211> LENGTH: 14
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (5)..(6)
<223> OTHER INFORMATION: 3' dithioate linkage
<220> FEATURE:
<221> NAME/KEY: misc_feature
<222> LOCATION: (9)..(10)
<223> OTHER INFORMATION: 3' dithioate linkage
<220> FEATURE:
<221> NAME/KEY: misc_feature
<222> LOCATION: (13)..(14)
<223> OTHER INFORMATION: 3' dithioate linkage

<400> SEQUENCE: 47

```
ccagtgactc agtg                                            14
```

<210> SEQ ID NO 48
<211> LENGTH: 14
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (3)..(4)
<223> OTHER INFORMATION: 3' dithioate linkage
<220> FEATURE:
<221> NAME/KEY: misc_feature
<222> LOCATION: (7)..(8)
<223> OTHER INFORMATION: 3' dithioate linkage
<220> FEATURE:
<221> NAME/KEY: misc_feature
<222> LOCATION: (11)..(12)
<223> OTHER INFORMATION: 3' dithioate linkage

<400> SEQUENCE: 48

```
cactgagtca ctgg                                            14
```

<210> SEQ ID NO 49
<211> LENGTH: 14
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (9)..(11)
<223> OTHER INFORMATION: 3' dithioate linkage

<400> SEQUENCE: 49

```
ccaggagatt ccac                                            14
```

<210> SEQ ID NO 50
<211> LENGTH: 14
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (1)..(2)
<223> OTHER INFORMATION: 3' dithioate linkage
<220> FEATURE:
<221> NAME/KEY: misc_feature -continued

```
<222> LOCATION: (6)..(7)
<223> OTHER INFORMATION: 3' dithioate linkage
<220> FEATURE:
<221> NAME/KEY: misc_feature
<222> LOCATION: (8)..(9)
<223> OTHER INFORMATION: 3' dithioate linkage
<220> FEATURE:
<221> NAME/KEY: misc_feature
<222> LOCATION: (11)..(12)
<223> OTHER INFORMATION: 3' dithioate linkage

<400> SEQUENCE: 50
gtggaatctc ctgg                                                     14

<210> SEQ ID NO 51
<211> LENGTH: 14
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (9)..(11)
<223> OTHER INFORMATION: 3' dithioate linkage

<400> SEQUENCE: 51
ccaggagatt ccac                                                     14

<210> SEQ ID NO 52
<211> LENGTH: 14
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (1)..(2)
<223> OTHER INFORMATION: 3' dithioate linkage
<220> FEATURE:
<221> NAME/KEY: misc_feature
<222> LOCATION: (6)..(7)
<223> OTHER INFORMATION: 3' dithioate linkage
<220> FEATURE:
<221> NAME/KEY: misc_feature
<222> LOCATION: (8)..(9)
<223> OTHER INFORMATION: 3' dithioate linkage
<220> FEATURE:
<221> NAME/KEY: misc_feature
<222> LOCATION: (11)..(12)
<223> OTHER INFORMATION: 3' dithioate linkage

<400> SEQUENCE: 52
gtggaatctc ctgg                                                     14

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 53
agttgagggg actttcccag gctt                                          24

<210> SEQ ID NO 54
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      polynucleotide sequence

<400> SEQUENCE: 54
gcctgggaaa gtcccctcaa ct                                              22

<210> SEQ ID NO 55
<211> LENGTH: 14
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (9)..(11)
<223> OTHER INFORMATION: 3' dithioate linkage

<400> SEQUENCE: 55
ccaggagatt ccac                                                       14

<210> SEQ ID NO 56
<211> LENGTH: 14
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (2)..(3)
<223> OTHER INFORMATION: 3' dithioate linkage
<220> FEATURE:
<221> NAME/KEY: misc_feature
<222> LOCATION: (7)..(8)
<223> OTHER INFORMATION: 3' dithioate linkage
<220> FEATURE:
<221> NAME/KEY: misc_feature
<222> LOCATION: (9)..(10)
<223> OTHER INFORMATION: 3' dithioate linkage
<220> FEATURE:
<221> NAME/KEY: misc_feature
<222> LOCATION: (12)..(13)
<223> OTHER INFORMATION: 3' dithioate linkage

<400> SEQUENCE: 56
gtggaatctc ctgg                                                       14

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (5)..(6)
<223> OTHER INFORMATION: 3' dithioate linkage
<220> FEATURE:
<221> NAME/KEY: misc_feature
<222> LOCATION: (9)..(11)
<223> OTHER INFORMATION: 3' dithioate linkage
<220> FEATURE:
<221> NAME/KEY: misc_feature
<222> LOCATION: (16)..(18)
<223> OTHER INFORMATION: 3' dithioate linkage

<400> SEQUENCE: 57
cgcccagtga aggtggaacc cc                                              22
```

-continued

```
<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (8)..(9)
<223> OTHER INFORMATION: 3' dithioate linkage
<220> FEATURE:
<221> NAME/KEY: misc_feature
<222> LOCATION: (14)..(15)
<223> OTHER INFORMATION: 3' dithioate linkage

<400> SEQUENCE: 58
ggggttccac cttcactggg cg                                              22

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (5)..(6)
<223> OTHER INFORMATION: 3' dithioate linkage
<220> FEATURE:
<221> NAME/KEY: misc_feature
<222> LOCATION: (9)..(10)
<223> OTHER INFORMATION: 3' dithioate linkage
<220> FEATURE:
<221> NAME/KEY: misc_feature
<222> LOCATION: (17)..(18)
<223> OTHER INFORMATION: 3' dithioate linkage

<400> SEQUENCE: 59
cgcccagtga aggtggaacc cc                                              22

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (8)..(9)
<223> OTHER INFORMATION: 3' dithioate linkage
<220> FEATURE:
<221> NAME/KEY: misc_feature
<222> LOCATION: (14)..(15)
<223> OTHER INFORMATION: 3' dithioate linkage

<400> SEQUENCE: 60
ggggttccac cttcactggg cg                                              22

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (5)..(6)
<223> OTHER INFORMATION: 3' dithioate linkage
```

```
<220> FEATURE:
<221> NAME/KEY: misc_feature
<222> LOCATION: (17)..(18)
<223> OTHER INFORMATION: 3' dithioate linkage

<400> SEQUENCE: 61
cgcccagtga aggtggaacc cc                                              22

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (8)..(9)
<223> OTHER INFORMATION: 3' dithioate linkage
<220> FEATURE:
<221> NAME/KEY: misc_feature
<222> LOCATION: (14)..(15)
<223> OTHER INFORMATION: 3' dithioate linkage

<400> SEQUENCE: 62
ggggttccac cttcactggg cg                                              22

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (5)..(6)
<223> OTHER INFORMATION: 3' dithioate linkage
<220> FEATURE:
<221> NAME/KEY: misc_feature
<222> LOCATION: (9)..(11)
<223> OTHER INFORMATION: 3' dithioate linkage
<220> FEATURE:
<221> NAME/KEY: misc_feature
<222> LOCATION: (16)..(18)
<223> OTHER INFORMATION: 3' dithioate linkage

<400> SEQUENCE: 63
cgcccagtga aggtggaacc cc                                              22

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 64
ggggttccac cttcactggg cg                                              22

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (5)..(6)
```

```
<223> OTHER INFORMATION: 3' dithioate linkage
<220> FEATURE:
<221> NAME/KEY: misc_feature
<222> LOCATION: (9)..(10)
<223> OTHER INFORMATION: 3' dithioate linkage
<220> FEATURE:
<221> NAME/KEY: misc_feature
<222> LOCATION: (17)..(18)
<223> OTHER INFORMATION: 3' dithioate linkage

<400> SEQUENCE: 65
cgcccagtga aggtggaacc cc                                              22

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 66
ggggttccac cttcactggg cg                                              22

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (5)..(6)
<223> OTHER INFORMATION: 3' dithioate linkage
<220> FEATURE:
<221> NAME/KEY: misc_feature
<222> LOCATION: (17)..(18)
<223> OTHER INFORMATION: 3' dithioate linkage

<400> SEQUENCE: 67
cgcccagtga aggtggaacc cc                                              22

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 68
ggggttccac cttcactggg cg                                              22

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic
      polynucleotide sequence

<400> SEQUENCE: 69
cgcccagtga aggtggaacc cc                                              22

<210> SEQ ID NO 70
<211> LENGTH: 22
<212> TYPE: DNA
<213> ORGANISM: Artificial Sequence
```

```
                                      -continued
<220> FEATURE:
<223> OTHER INFORMATION: Description of Artificial Sequence: Synthetic
      polynucleotide sequence
<220> FEATURE:
<221> NAME/KEY: misc_feature
<222> LOCATION: (8)..(9)
<223> OTHER INFORMATION: 3' dithioate linkage
<220> FEATURE:
<221> NAME/KEY: misc_feature
<222> LOCATION: (14)..(15)
<223> OTHER INFORMATION: 3' dithioate linkage

<400> SEQUENCE: 70
ggggttccac cttcactggg cg                                         22
```